(12) United States Patent
Boudet et al.

(10) Patent No.: US 6,211,432 B1
(45) Date of Patent: Apr. 3, 2001

(54) DNA SEQUENCES CODING FOR A CINNAMOYL COA REDUCTASE, AND APPLICATIONS THEREOF IN THE CONTROL OF LIGNIN CONTENTS IN PLANTS

(75) Inventors: Alain-Michel Boudet, Toulouse; Magalle Pichon; Jacqueline Grima-Pettenati, both of Fourqueveaux; Michel Beckert, Cournon d'Auvergne; Pascal Gamas, L'Union; Jean-François Briat, St Clement de Riviere, all of (FR)

(73) Assignees: Centre National de la Recherche Scientifique; Institut National de la Recherche Agronomique, both of Paris (FR)

(*) Notice: Subject to any disclaimer, the term of this patent is extended or adjusted under 35 U.S.C. 154(b) by 0 days.

(21) Appl. No.: 09/043,937

(22) PCT Filed: Oct. 3, 1996

(86) PCT No.: PCT/FR96/01544

§ 371 Date: Jul. 24, 1998

§ 102(e) Date: Jul. 24, 1998

(87) PCT Pub. No.: WO97/12782

PCT Pub. Date: Apr. 10, 1997

(30) Foreign Application Priority Data

Oct. 3, 1995 (FR) .................................................. 95 11623

(51) Int. Cl.[7] .............................. A01H 1/00; A01H 9/00; A01H 5/00; C12N 15/82; C12N 15/87
(52) U.S. Cl. ........................ 800/278; 435/69.1; 435/70.1; 435/71.1; 435/466; 435/410; 435/418; 435/419; 435/320.1; 536/23.1; 536/23.6; 800/284; 800/288; 800/290; 800/295; 800/298; 800/320.1
(58) Field of Search .................................. 435/69.1, 70.1, 435/71.1, 466, 410, 418, 419, 320.1; 536/23.1, 23.6; 800/278, 284, 288, 290, 295, 298, 320.1

(56) References Cited

FOREIGN PATENT DOCUMENTS

| | | |
|---|---|---|
| 0 155 872 | 9/1985 | (EP) . |
| WO9305159 * | 3/1993 | (WO) . |
| WO 93 05159 | 3/1993 | (WO) . |
| WO 95 27790 | 10/1995 | (WO) . |

OTHER PUBLICATIONS

Smith et al. Nature. 1988. vol. 334: 724–726, 1988.*
Theoretical and Applied Genetics, vol. 87, No. 8, pp. 1006–1015, XP002006034 Carron, T.R., Et Al.: "Genetic Modification of Condensed Tannin Biosynthesis in Lotus Corniculatus.1. Heterologous Antisense Dihydroflavonol Reductase Down–Regulates Tannin Accumulation in "Hairy Root" Cultures" see the entire document..

Bull. Liason—Groupe Polyphenols, vol. 16(PT.2), pp. 295–300, XP002006035 Robbins, M.P., Et Al.: "Manipulation of Condensed Tannin Biosynthesis in Forage Legumes" see p. 296.

J. Cell. Biochem. Suppl., vol. 17A, p. 26 XP002006036 Campbell, M.M., Et Al.: "Hydroxycinnamoyl–coA reductase from Eucalyptus. Molecular analysis of a key control point of lignification" *abtégé A 305 * & Keystone Symposium on the Extracellular Matrix of Plants: Molecular, Cellular and Developmental Biology, Sant Fe, New Mexico, USA, Jan. 9–15, 1993.

New Phytologist 129 (2). 1995. 203–236., XP002006037 Boudet A M Et Al: "Tansley review No. 80: Biochemistry and molecular biology of lignification." See p. 221.

Plant Physiology (Rockville) 106 (2). Oct. 1994. 625–632., XP002006038 Goffner D Et Al: "Purification and characterization of cinnamoyl–coenzyme A:NADP oxidoreductase in *Eucalyptus gunnii*." See the entire document.

Abstr.Pap.Am.Chem.Soc.;(1996) 211 Meet., Pt.1, CHED274 DEN: ASCRAL ISSN: 0065–7727 1TH ACS National Meeting, New Orleans, LA, Mar. 24–28, 1996., XP000618488 Boudet A M: "Genes involved in monolignol biosynthesis and their manipulation for tailoring new lignins" see abstract.

EMBL Sequence Database. REL. 43. Accession No. D46598. Mar. 9, 1995., XP002025776 Sasaki, T., Et Al.: "Rice cDNA, partial sequence (S11367–1A)" see sequence.

EMBL Sequence Database. REL. 42. Accession No. T41765. Jan. 31, 1995, XP002025777 Newman, T., Et Al.: "10346 Arabidopsis thaliana cDNA clone 67E6T7" see sequence.

Plant Physiology, vol. 96, 1991, pp. 577–583, XP002025778 Lagrimini, L.M.: "Wound–induced deposition of polyphenols in transgenic plants overexpressing peroxidase" see the entire document.

Eur. J. Biochem. 139, 259–265(1984) FEBS 1984; Purification and properties of cinnamoyl–CoA reductase and cinnamyl alcohol dehydrogenase from poplar stems (*Populus X euramericana*) Farid Sarni et al.

* cited by examiner

Primary Examiner—Paula K. Hutzell
Assistant Examiner—Ousama Zaghmout
(74) Attorney, Agent, or Firm—Nixon & Vanderhye P.C.

(57) ABSTRACT

The present invention relates to any DNA sequence comprising as a coding region all or part of the nucleotidic sequence coding for a mRNA coding coding for a cinnamoyl CoA reductase (CCR) in lucern and/or corn, or all or part of the nucleotide sequence complementary of the latter and coding for an antisense mRNA susceptible of hybridizing with said mRNA. The invention also relates to the use of said sequences for implementing processes for the regulation of lignin biosynthesis in plants.

14 Claims, 4 Drawing Sheets

Figure 1:
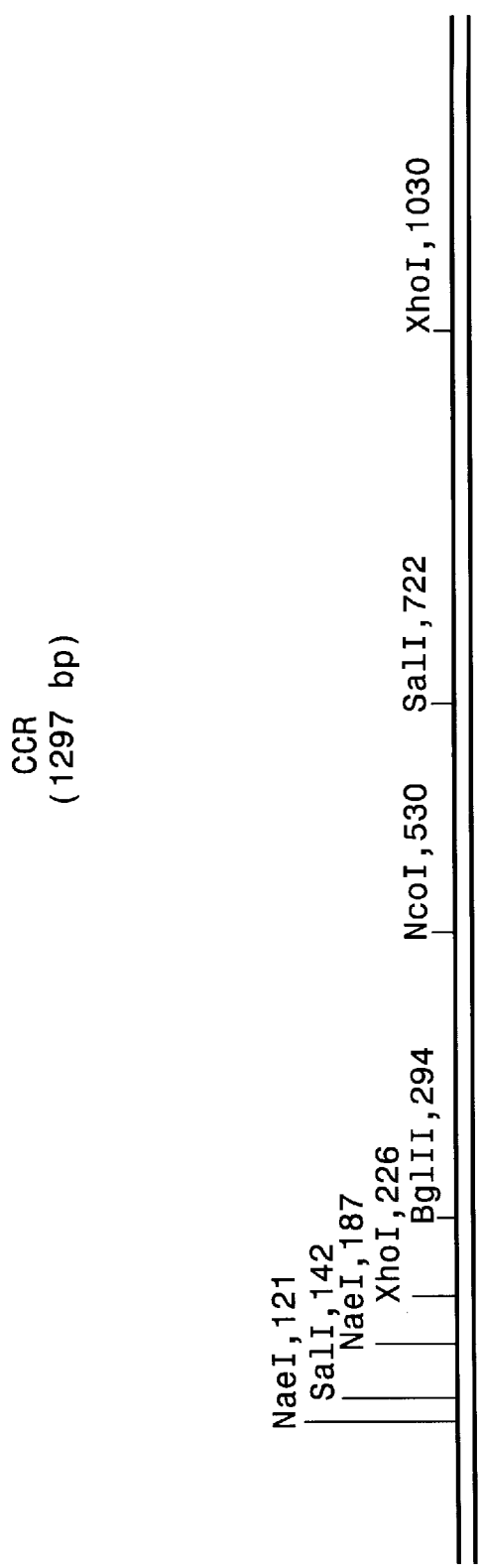

SEQUENCE LISTING (1) GENERAL INFORMATION:

(iii) NUMBER OF SEQUENCES: 29

(2) INFORMATION FOR SEQ ID NO: 1:

(i) SEQUENCE CHARACTERISTICS:
      (A) LENGTH: 1568 base pairs
      (B) TYPE: nucleic acid
      (C) STRANDEDNESS: double
      (D) TOPOLOGY: linear (ii) MOLECULE TYPE: cDNA to mRNA (ix) FEATURE:
      (A) NAME/KEY: CDS
      (B) LOCATION: 278..1306

(xi) SEQUENCE DESCRIPTION: SEQ ID NO: 1:

```
CATGATTACG CCAAGCTCGA AATTAACCCT CACTAAAGGG AACAAAAGCT GGAGCTCCAC        60

CGCGGTGGCG GCCGCTCTAG AACTAGTGGA TCCCCCGGGC TGCAGGAATT CGGCACGAG        120

GGATAGAGAA GAAAGGTGGT CATATTTCCC ACTTATTATT ACAAAGTAAC GTCACACCA        180

CTTTATCACC ACCTTTCTTC TCTATCCCAT TCATTCTCAT TCATTCATTC ACCTCACCT        240

ACCTCACCTC ACCTCCCTTT ACAAGAAGAA GGAATAT ATG CCT GCC GCT ACC GCA        295
                                         Met Pro Ala Ala Thr Ala
                                           1               5

GCC GCC GCC GCC GAA TCT TCC TCA GTT TCC GGC GAA ACC ATA TGT GTC        343
Ala Ala Ala Ala Glu Ser Ser Ser Val Ser Gly Glu Thr Ile Cys Val
             10                  15                  20

ACC GGG GCC GGT GGC CTC ATC GCT TCT TGG ATG GTT AAG CTC CTC TTG        391
Thr Gly Ala Gly Gly Leu Ile Ala Ser Trp Met Val Lys Leu Leu Leu
         25                  30                  35

GAG AAA GGC TAT ACC GTT CGA GGA ACC TTG CGA AAC CCA GAT GAT CCA        439
Glu Lys Gly Tyr Thr Val Arg Gly Thr Leu Arg Asn Pro Asp Asp Pro
     40                  45                  50

AAA AAT GGG CAC TTG AAA AAG TTG GAA GGA GCA AAA GAA AGG CTA ACT        487
Lys Asn Gly His Leu Lys Lys Leu Glu Gly Ala Lys Glu Arg Leu Thr
 55                  60                  65                  70

TTG GTC AAA GTT GAT CTC CTT GAT CTT AAC TCC GTT AAA GAA GCT GTT        535
Leu Val Lys Val Asp Leu Leu Asp Leu Asn Ser Val Lys Glu Ala Val
                 75                  80                  85

AAT GGA TGT CAT GGT GTC TTT CAC ACT GCT TCT CCC GTT ACA GAT AAC        583
Asn Gly Cys His Gly Val Phe His Thr Ala Ser Pro Val Thr Asp Asn
             90                  95                 100
```

```
CCC GAG GAA ATG GTG GAG CCA GCA GTG AAT GGA GCA AAG AAT GTG ATC         631
Pro Glu Glu Met Val Glu Pro Ala Val Asn Gly Ala Lys Asn Val Ile
        105                 110                 115

ATA GCT GGT GCA GAA GCA AAA GTG AGG CGC GTG GTT TTC ACA TCA TCA         679
Ile Ala Gly Ala Glu Ala Lys Val Arg Arg Val Val Phe Thr Ser Ser
120                 125                 130

ATT GGT GCA GTC TAT ATG GAC CCC AAT AGG AGT GTT GAT GTA GAG GTT         727
Ile Gly Ala Val Tyr Met Asp Pro Asn Arg Ser Val Asp Val Glu Val
135                 140                 145                 150

GAT GAG TCT TGC TGG AGT GAT TTG GAG TTT TGC AAG AAA ACC AAG AAT         775
Asp Glu Ser Cys Trp Ser Asp Leu Glu Phe Cys Lys Lys Thr Lys Asn
                155                 160                 165

TGG TAT TGC TAT GGG AAA GCA GTG GCA GAA GCA GCA TGG GAT GTA             823
Trp Tyr Cys Tyr Gly Lys Ala Val Ala Glu Ala Ala Trp Asp Val
                170                 175                 180

GCA AAA GAG AAA GGT GTG GAT TTG GTT GTA GTG AAT CCA GTT TTG GTT         871
Ala Lys Glu Lys Gly Val Asp Leu Val Val Val Asn Pro Val Leu Val
            185                 190                 195

CTT GGA CCA TTG CTA CAA CCT ACA ATC AAT GCA AGC ACA ATT CAC ATA         919
Leu Gly Pro Leu Leu Gln Pro Thr Ile Asn Ala Ser Thr Ile His Ile
        200                 205                 210

CTA AAA TAC CTA ACT GGT TCA GCT AAG ACC TAT GCA AAT GCA ACA CAA         967
Leu Lys Tyr Leu Thr Gly Ser Ala Lys Thr Tyr Ala Asn Ala Thr Gln
215                 220                 225                 230

GCT TAT GTT CAT GTT AGG GAT GTT GCA TTA GCT CAC ATA CTT GTT TAT        1015
Ala Tyr Val His Val Arg Asp Val Ala Leu Ala His Ile Leu Val Tyr
                235                 240                 245

GAG AAA CCT TCT GCT TCT GGT AGA TAC TTA TGT GCT GAA ACT TCA CTT        1063
Glu Lys Pro Ser Ala Ser Gly Arg Tyr Leu Cys Ala Glu Thr Ser Leu
                250                 255                 260

CAT CGT GGG GAG CTT GTT GAA ATT CTT GCT AAG TAT TTC CCT GAG TAC        1111
His Arg Gly Glu Leu Val Glu Ile Leu Ala Lys Tyr Phe Pro Glu Tyr
            265                 270                 275

CCA ATT CCT ACC AAG TGT TCA GAT GAA AAG AAT CCT CGA GTG AAA CCA        1159
Pro Ile Pro Thr Lys Cys Ser Asp Glu Lys Asn Pro Arg Val Lys Pro
        280                 285                 290

CAT ATC TTC TCA AAT AAA AAA CTG AAG GAT TTG GGA TTG GAA TTT ACA        1207
His Ile Phe Ser Asn Lys Lys Leu Lys Asp Leu Gly Leu Glu Phe Thr
295                 300                 305                 310

CCA GTG AGT GAA TGT TTA TAT GAA ACC GTT AAG AGC CTA CAA GAC CAA        1255
Pro Val Ser Glu Cys Leu Tyr Glu Thr Val Lys Ser Leu Gln Asp Gln
                315                 320                 325

GGT CAC CTT TCT ATT CCA AAC AAA GAA GAT TCT CTA GCA GTC AAA TCC        1303
Gly His Leu Ser Ile Pro Asn Lys Glu Asp Ser Leu Ala Val Lys Ser
                330                 335                 340

TAAACCAACC ATCCTTTGTT AACAAGTTCA ATTCAGGGCC AAAAGAATC ATCTTTTA        1363

TACCTGCGAG GCTTTAGGCT CTAGCAATTT GATACTATAA ATGACCGTAA TTGGATGG       1423

AGTTGTAAGA AAGTATCATG CTAGAATTTA CTATTTGTCT TTATGTTTGA AAAATAAG       1483

CATTATATTA AAAAAAAAAA AAAAAAAAAA AACTCGAGGG GGGGCCCGGT ACCCAATT       1543

CCCTATAGTG AGTCGTATTA CAATT                                            1568

(2) INFORMATION FOR SEQ ID NO: 2:

(i) SEQUENCE CHARACTERISTICS:
        (A) LENGTH: 342 amino acids
        (B) TYPE: amino acid
        (D) TOPOLOGY: linear
```

(ii) MOLECULE TYPE: protein (xi) SEQUENCE DESCRIPTION: SEQ ID NO: 2:

Met Pro Ala Ala Thr Ala Ala Ala Ala Glu Ser Ser Ser Val Ser
 1               5                  10                  15

Gly Glu Thr Ile Cys Val Thr Gly Ala Gly Gly Leu Ile Ala Ser Trp
            20                  25                  30

Met Val Lys Leu Leu Leu Glu Lys Gly Tyr Thr Val Arg Gly Thr Leu
        35                  40                  45

Arg Asn Pro Asp Asp Pro Lys Asn Gly His Leu Lys Lys Leu Glu Gly
    50                  55                  60

Ala Lys Glu Arg Leu Thr Leu Val Lys Val Asp Leu Leu Asp Leu Asn
 65                  70                  75                  80

Ser Val Lys Glu Ala Val Asn Gly Cys His Gly Val Phe His Thr Ala
                85                  90                  95

Ser Pro Val Thr Asp Asn Pro Glu Glu Met Val Glu Pro Ala Val Asn
            100                 105                 110

Gly Ala Lys Asn Val Ile Ile Ala Gly Ala Glu Ala Lys Val Arg Arg
        115                 120                 125

Val Val Phe Thr Ser Ser Ile Gly Ala Val Tyr Met Asp Pro Asn Arg
    130                 135                 140

Ser Val Asp Val Glu Val Asp Glu Ser Cys Trp Ser Asp Leu Glu Phe
145                 150                 155                 160

Cys Lys Lys Thr Lys Asn Trp Tyr Cys Tyr Gly Lys Ala Val Ala Glu
                165                 170                 175

Ala Ala Ala Trp Asp Val Ala Lys Glu Lys Gly Val Asp Leu Val Val
            180                 185                 190

Val Asn Pro Val Leu Val Leu Gly Pro Leu Leu Gln Pro Thr Ile Asn
        195                 200                 205

Ala Ser Thr Ile His Ile Leu Lys Tyr Leu Thr Gly Ser Ala Lys Thr
    210                 215                 220

Tyr Ala Asn Ala Thr Gln Ala Tyr Val His Val Arg Asp Val Ala Leu
225                 230                 235                 240

Ala His Ile Leu Val Tyr Glu Lys Pro Ser Ala Ser Gly Arg Tyr Leu
                245                 250                 255

Cys Ala Glu Thr Ser Leu His Arg Gly Glu Leu Val Glu Ile Leu Ala
            260                 265                 270

Lys Tyr Phe Pro Glu Tyr Pro Ile Pro Thr Lys Cys Ser Asp Glu Lys
        275                 280                 285

Asn Pro Arg Val Lys Pro His Ile Phe Ser Asn Lys Lys Leu Lys Asp
    290                 295                 300

Leu Gly Leu Glu Phe Thr Pro Val Ser Glu Cys Leu Tyr Glu Thr Val
305                 310                 315                 320

Lys Ser Leu Gln Asp Gln Gly His Leu Ser Ile Pro Asn Lys Glu Asp
                325                 330                 335

Ser Leu Ala Val Lys Ser
            340

(2) INFORMATION FOR SEQ ID NO: 3:

(i) SEQUENCE CHARACTERISTICS:
        (A) LENGTH: 1556 base pairs
        (B) TYPE: nucleic acid
        (C) STRANDEDNESS: double
        (D) TOPOLOGY: linear (ii) MOLECULE TYPE: cDNA to mRNA (ix) FEATURE:
    (A) NAME/KEY: CDS
    (B) LOCATION: 195..1310

(xi) SEQUENCE DESCRIPTION: SEQ ID NO: 3:

```
GTTCCCATGA TTACGCCAAG CTCGAAATTA ACCCTCACTA AAGGGAACAA AAGCTGGAGC      60

TCCACCGCGG TGGCGGCCGC TCTAGAACTA GTGGATCCCC CGGGCTGCAG GAATTCGGC      120

CGAGAGGACA CAAGCGAGCG CTAGCCAGAA GAGCAGCTGC AGGTACTATT ATCATCGTC      180

TCGTCGTCGC CAGG ATG ACC GTC GTC GAC GCC GTC GTC TCC TCC ACC GAT      230
              Met Thr Val Val Asp Ala Val Val Ser Ser Thr Asp
               1               5                  10

GCC GGC GCC CCT GCC GCC GCC GCC GCA CCG GTA CCG GCG GGG AAC GGG      278
Ala Gly Ala Pro Ala Ala Ala Ala Ala Pro Val Pro Ala Gly Asn Gly
             15                  20                  25

CAG ACC GTG TGC GTC ACC GGC GCG GCC GGG TAC ATC GCC TCG TGG TTG      326
Gln Thr Val Cys Val Thr Gly Ala Ala Gly Tyr Ile Ala Ser Trp Leu
         30                  35                  40

GTG AAG CTG CTG CTC GAG AAG GGA TAC ACT GTG AAG GGC ACC GTG AGG      374
Val Lys Leu Leu Leu Glu Lys Gly Tyr Thr Val Lys Gly Thr Val Arg
 45                  50                  55                  60

AAC CCA GAT GAC CCG AAG AAC GCG CAC CTC AGG GCG CTG GAC GGC GCC      422
Asn Pro Asp Asp Pro Lys Asn Ala His Leu Arg Ala Leu Asp Gly Ala
                 65                  70                  75

GCC GAG CGG CTG ATC CTC TGC AAG GCC GAT CTG CTG GAC TAC GAC GCC      470
Ala Glu Arg Leu Ile Leu Cys Lys Ala Asp Leu Leu Asp Tyr Asp Ala
             80                  85                  90

ATC TGC CGC GCC GTG CAG GGC TGC CAG GGC GTC TTC CAC ACC GCC TCC      518
Ile Cys Arg Ala Val Gln Gly Cys Gln Gly Val Phe His Thr Ala Ser
         95                  100                 105

CCC GTC ACC GAC GAC CCG GAG CAA ATG GTG GAG CCG GCG GTG CGC GGC      566
Pro Val Thr Asp Asp Pro Glu Gln Met Val Glu Pro Ala Val Arg Gly
     110                 115                 120

ACC GAG TAC GTG ATC AAC GCG GCG GCG GAG GCC GGC ACG GTG CGG CGG      614
Thr Glu Tyr Val Ile Asn Ala Ala Ala Glu Ala Gly Thr Val Arg Arg
125                 130                 135                 140

GTG GTG TTC ACG TCG TCC ATC GGC GCC GTG ACC ATG GAC CCC AAG CGC      662
Val Val Phe Thr Ser Ser Ile Gly Ala Val Thr Met Asp Pro Lys Arg
                145                 150                 155

GGG CCC GAC GTC GTG GTC GAC GAG TCG TGC TGG AGC GAC CTC GAG TTC      710
Gly Pro Asp Val Val Val Asp Glu Ser Cys Trp Ser Asp Leu Glu Phe
            160                 165                 170

TGC GAG AAA ACC AGG AAC TGG TAC TGC TAC GGC AAG GCG GTG GCG GAG      758
Cys Glu Lys Thr Arg Asn Trp Tyr Cys Tyr Gly Lys Ala Val Ala Glu
        175                 180                 185

CAG GCG GCG TGG GAG GCG GCC CGG CGG CGG GGC GTG GAC CTG GTG GTG      806
Gln Ala Ala Trp Glu Ala Ala Arg Arg Arg Gly Val Asp Leu Val Val
    190                 195                 200

GTG AAC CCC GTG CTG GTG GTG GGC CCC CTG CTG CAG GCG ACG GTG AAC      854
Val Asn Pro Val Leu Val Val Gly Pro Leu Leu Gln Ala Thr Val Asn
205                 210                 215                 220

GCC AGC ATC GCG CAC ATC CTC AAG TAC CTG GAC GGC TCG GCC CGC ACC      902
Ala Ser Ile Ala His Ile Leu Lys Tyr Leu Asp Gly Ser Ala Arg Thr
                225                 230                 235

TTC GCC AAC GCC GTG CAG GCG TAC GTG GAC GTG CGC GAC GTG GCC GAC      950
Phe Ala Asn Ala Val Gln Ala Tyr Val Asp Val Arg Asp Val Ala Asp
            240                 245                 250

GCG CAC CTC CGC GTC TTC GAG AGC CCC CGC GCG TCC GGC CGC CAC CTC      998
```

-continued

```
                    Ala His Leu Arg Val Phe Glu Ser Pro Arg Ala Ser Gly Arg His Leu
                                    255                 260                 265

TGC GCC GAG CGC GTC CTC CAC CGC GAG GAC GTC GTC CGC ATC CTC GCC          1046
Cys Ala Glu Arg Val Leu His Arg Glu Asp Val Val Arg Ile Leu Ala
270                 275                 280

AAG CTC TTC CCC GAG TAC CCC GTC CCA GCC AGG TGC TCC GAC GAG GTG          1094
Lys Leu Phe Pro Glu Tyr Pro Val Pro Ala Arg Cys Ser Asp Glu Val
285                 290                 295                 300

AAT CCG CGG AAG CAG CCG TAC AAG TTC TCC AAC CAG AAG CTC CGG GAC          1142
Asn Pro Arg Lys Gln Pro Tyr Lys Phe Ser Asn Gln Lys Leu Arg Asp
                    305                 310                 315

CTG GGG CTG CAG TTC CGG CCG GTC AGC CAG TCG CTT TAC GAC ACG GTG          1190
Leu Gly Leu Gln Phe Arg Pro Val Ser Gln Ser Leu Tyr Asp Thr Val
                320                 325                 330

AAG AAC CTC CAG GAG AAG GGC CAC CTG CCG GTG CTC GGA GAG CGG ACG          1238
Lys Asn Leu Gln Glu Lys Gly His Leu Pro Val Leu Gly Glu Arg Thr
            335                 340                 345

ACG ACG GAG GCC GCC GAC AAG GAT GCC CCC GCG GCC GAG ATG CAG CAG          1286
Thr Thr Glu Ala Ala Asp Lys Asp Ala Pro Ala Ala Glu Met Gln Gln
350                 355                 360

GGA GGG ATC GCC ATC CGT GCC TGAGAGGGCG ATGCCACACA TGAACACCAA             1337
Gly Gly Ile Ala Ile Arg Ala
365                 370

AGCAATGTTC ATACTGCTGC CCTGCACCTG CACCTTCCCC TGCTGTGTAA ACAGGCCT          1397

GTTTGTTCTG GCTGATAGTG ATGTACCCTA AGACTTGTAA CGTCATGTTC GTTCTTGT          1457

ACTATAGCGA GTGAATAAAA TTGGTTAATG TTGGATAATT CCAAAAAAAA AAAAAAA           1517

CTCGAGGGGG GGCCCGGTAC CCAATTCGCC CTATAGTGA                               1556
```

(2) INFORMATION FOR SEQ ID NO: 4:

(i) SEQUENCE CHARACTERISTICS:
        (A) LENGTH: 371 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Thr Val Val Asp Ala Val Ser Ser Thr Asp Ala Gly Ala Pro
1               5                   10                  15

Ala Ala Ala Ala Ala Pro Val Pro Ala Gly Asn Gly Gln Thr Val Cys
                20                  25                  30

Val Thr Gly Ala Ala Gly Tyr Ile Ala Ser Trp Leu Val Lys Leu Leu
            35                  40                  45

Leu Glu Lys Gly Tyr Thr Val Lys Gly Thr Val Arg Asn Pro Asp Asp
    50                  55                  60

Pro Lys Asn Ala His Leu Arg Ala Leu Asp Gly Ala Ala Glu Arg Leu
65                  70                  75                  80

Ile Leu Cys Lys Ala Asp Leu Leu Asp Tyr Asp Ala Ile Cys Arg Ala
                85                  90                  95

Val Gln Gly Cys Gln Gly Val Phe His Thr Ala Ser Pro Val Thr Asp
            100                 105                 110

Asp Pro Glu Gln Met Val Glu Pro Ala Val Arg Gly Thr Glu Tyr Val
        115                 120                 125

Ile Asn Ala Ala Ala Glu Ala Gly Thr Val Arg Arg Val Val Phe Thr
    130                 135                 140

Ser Ser Ile Gly Ala Val Thr Met Asp Pro Lys Arg Gly Pro Asp Val
```

```
145                 150                 155                 160
Val Val Asp Glu Ser Cys Trp Ser Asp Leu Glu Phe Cys Glu Lys Thr
                165                 170                 175

Arg Asn Trp Tyr Cys Tyr Gly Lys Ala Val Ala Glu Gln Ala Ala Trp
                180                 185                 190

Glu Ala Ala Arg Arg Arg Gly Val Asp Leu Val Val Val Asn Pro Val
            195                 200                 205

Leu Val Val Gly Pro Leu Leu Gln Ala Thr Val Asn Ala Ser Ile Ala
        210                 215                 220

His Ile Leu Lys Tyr Leu Asp Gly Ser Ala Arg Thr Phe Ala Asn Ala
225                 230                 235                 240

Val Gln Ala Tyr Val Asp Val Arg Asp Val Ala Asp Ala His Leu Arg
                245                 250                 255

Val Phe Glu Ser Pro Arg Ala Ser Gly Arg His Leu Cys Ala Glu Arg
                260                 265                 270

Val Leu His Arg Glu Asp Val Val Arg Ile Leu Ala Lys Leu Phe Pro
            275                 280                 285

Glu Tyr Pro Val Pro Ala Arg Cys Ser Asp Glu Val Asn Pro Arg Lys
        290                 295                 300

Gln Pro Tyr Lys Phe Ser Asn Gln Lys Leu Arg Asp Leu Gly Leu Gln
305                 310                 315                 320

Phe Arg Pro Val Ser Gln Ser Leu Tyr Asp Thr Val Lys Asn Leu Gln
                325                 330                 335

Glu Lys Gly His Leu Pro Val Leu Gly Glu Arg Thr Thr Glu Ala
            340                 345                 350

Ala Asp Lys Asp Ala Pro Ala Ala Glu Met Gln Gln Gly Gly Ile Ala
        355                 360                 365

Ile Arg Ala
    370

(2) INFORMATION FOR SEQ ID NO: 5:

(i) SEQUENCE CHARACTERISTICS:
        (A) LENGTH: 1297 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 136..1140

(xi) SEQUENCE DESCRIPTION: SEQ ID NO: 5:

CGGCCGGGAC GACCCGTTCC TCTTCTTCCG GGTCACCGTC ACCATGTTAC ACAACATCTC      60

CGGCTAAAAA AAAAAGGAAA AAAAGCGCAA CCTCCACCTC CTGAACCCCT CTCCCCCCT     120

GCCGGCAATC CCACC ATG CCC GTC GAC GCC CTC CCC GGT TCC GGC CAG ACC     171
                 Met Pro Val Asp Ala Leu Pro Gly Ser Gly Gln Thr
                  1               5                  10

GTC TGC GTC ACC GGC GCC GGC GGG TTC ATC GCC TCC TGG ATT GTC AAG     219
Val Cys Val Thr Gly Ala Gly Gly Phe Ile Ala Ser Trp Ile Val Lys
         15                  20                  25

CTT CTC CTC GAG CGA GGC TAC ACC GTG CGA GGA ACC GTC AGG AAC CCA     267
Leu Leu Leu Glu Arg Gly Tyr Thr Val Arg Gly Thr Val Arg Asn Pro
     30                  35                  40

GAC GAC CCG AAG AAT GGT CAT CTG AGA GAT CTG GAA GGA GCC AGC GAG     315
Asp Asp Pro Lys Asn Gly His Leu Arg Asp Leu Glu Gly Ala Ser Glu
```

-continued

```
                 45                      50                      55                      60
AGG CTG ACG CTG TAC AAG GGT GAT CTG ATG GAC TAC GGG AGC TTG GAA                                363
Arg Leu Thr Leu Tyr Lys Gly Asp Leu Met Asp Tyr Gly Ser Leu Glu
                         65                      70                      75

GAA GCC ATC AAG GGG TGC GAC GGC GTC GTC CAC ACC GCC TCT CCG GTC                                411
Glu Ala Ile Lys Gly Cys Asp Gly Val Val His Thr Ala Ser Pro Val
                 80                      85                      90

ACC GAC GAT CCT GAG CAA ATG GTG GAG CCA GCG GTG ATC GGG ACG AAA                                459
Thr Asp Asp Pro Glu Gln Met Val Glu Pro Ala Val Ile Gly Thr Lys
             95                     100                     105

AAT GTG ATC GTC GCA GCG GCG GAG GCC AAG GTC CGG CGG GTT GTG TTC                                507
Asn Val Ile Val Ala Ala Ala Glu Ala Lys Val Arg Arg Val Val Phe
        110                     115                     120

ACC TCC TCC ATC GGT GCA GTC ACC ATG GAC CCC AAC CGG GCA GAC GTT                                555
Thr Ser Ser Ile Gly Ala Val Thr Met Asp Pro Asn Arg Ala Asp Val
125                     130                     135                     140

GTG GTG GAC GAG TCT TGT TGG AGC GAC CTC GAA TTT TGC AAG AGC ACT                                603
Val Val Asp Glu Ser Cys Trp Ser Asp Leu Glu Phe Cys Lys Ser Thr
                    145                     150                     155

AAG AAC TGG TAT TGC TAC GGC AAG GCA GTG GCG GAG AAG GCC GCT TGG                                651
Lys Asn Trp Tyr Cys Tyr Gly Lys Ala Val Ala Glu Lys Ala Ala Trp
                160                     165                     170

CCA GAG GGC AAG GAG AGA GGG GTT GAC CTC GTG GTG ATT AAC CCT GTG                                699
Pro Glu Gly Lys Glu Arg Gly Val Asp Leu Val Val Ile Asn Pro Val
            175                     180                     185

CTC GTG CTT GGA CCG CTC CTT CAG TCG ACG ATC AAT GCG AGC ATC ATC                                747
Leu Val Leu Gly Pro Leu Leu Gln Ser Thr Ile Asn Ala Ser Ile Ile
        190                     195                     200

CAC ATC CTC AAG TAC TTG ACT GGC TCA GCC AAG ACC TAC GCC AAC TCG                                795
His Ile Leu Lys Tyr Leu Thr Gly Ser Ala Lys Thr Tyr Ala Asn Ser
205                     210                     215                     220

GTC CAG GCG TAC GTG CAC GTC AAG GAC GTC GCG CTT GCC CAC GTC CTT                                843
Val Gln Ala Tyr Val His Val Lys Asp Val Ala Leu Ala His Val Leu
                    225                     230                     235

GTC TTG GAG ACC CCA TCC GCC TCA GGC CGC TAT TTG TGC GCC GAG AGC                                891
Val Leu Glu Thr Pro Ser Ala Ser Gly Arg Tyr Leu Cys Ala Glu Ser
                240                     245                     250

GTC CTC CAC CGT GGC GAT GTG GTG GAA ATC CTT GCC AAG TTC TTC CCT                                939
Val Leu His Arg Gly Asp Val Val Glu Ile Leu Ala Lys Phe Phe Pro
            255                     260                     265

GAG TAT AAT GTA CCG ACC AAG TGC TCT GAT GAG GTG AAC CCA AGA GTA                                987
Glu Tyr Asn Val Pro Thr Lys Cys Ser Asp Glu Val Asn Pro Arg Val
        270                     275                     280

AAA CCA TAC AAG TTC TCC AAC CAG AAG CTG AGA GAC TTG GGG CTC GAG                                1035
Lys Pro Tyr Lys Phe Ser Asn Gln Lys Leu Arg Asp Leu Gly Leu Glu
285                     290                     295                     300

TTC ACC CCG GTG AAG CAG TGC CTG TAC GAA ACT GTC AAG AGC TTG CAG                                1083
Phe Thr Pro Val Lys Gln Cys Leu Tyr Glu Thr Val Lys Ser Leu Gln
                    305                     310                     315

GAG AAA GGC CAC CTA CCA GTC CCC TCC CCG CCG GAA GAT TCG GTG CGT                                1131
Glu Lys Gly His Leu Pro Val Pro Ser Pro Pro Glu Asp Ser Val Arg
                320                     325                     330

ATT CAG GGA TGATCTTAGA TCCATCACGG TGCGCATTTG TAATCCGGAG                                        1180
Ile Gln Gly
        335

AAATGAGAGA AACATGTGGG AATTTGTTTG TACTTTTCTA AGTCAAACCT GGAGATAC                                1240

ACCCTGAGTT CTGCATTGGA ATGGAAGTTG TCAATTGTTC CAAAAAAAAA AAAAAAA                                 1297
```

-continued (2) INFORMATION FOR SEQ ID NO: 6:

(i) SEQUENCE CHARACTERISTICS:
        (A) LENGTH: 335 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Pro Val Asp Ala Leu Pro Gly Ser Gly Gln Thr Val Cys Val Thr
 1               5                  10                  15

Gly Ala Gly Gly Phe Ile Ala Ser Trp Ile Val Lys Leu Leu Leu Glu
                20                  25                  30

Arg Gly Tyr Thr Val Arg Gly Thr Val Arg Asn Pro Asp Asp Pro Lys
            35                  40                  45

Asn Gly His Leu Arg Asp Leu Glu Gly Ala Ser Glu Arg Leu Thr Leu
 50                  55                  60

Tyr Lys Gly Asp Leu Met Asp Tyr Gly Ser Leu Glu Ala Ile Lys
 65                  70                  75                  80

Gly Cys Asp Gly Val Val His Thr Ala Ser Pro Val Thr Asp Asp Pro
                85                  90                  95

Glu Gln Met Val Glu Pro Ala Val Ile Gly Thr Lys Asn Val Ile Val
               100                 105                 110

Ala Ala Ala Glu Ala Lys Val Arg Arg Val Val Phe Thr Ser Ser Ile
           115                 120                 125

Gly Ala Val Thr Met Asp Pro Asn Arg Ala Asp Val Val Val Asp Glu
       130                 135                 140

Ser Cys Trp Ser Asp Leu Glu Phe Cys Lys Ser Thr Lys Asn Trp Tyr
145                 150                 155                 160

Cys Tyr Gly Lys Ala Val Ala Glu Lys Ala Ala Trp Pro Gly Lys
               165                 170                 175

Glu Arg Gly Val Asp Leu Val Val Ile Asn Pro Val Leu Val Leu Gly
           180                 185                 190

Pro Leu Leu Gln Ser Thr Ile Asn Ala Ser Ile Ile His Ile Leu Lys
       195                 200                 205

Tyr Leu Thr Gly Ser Ala Lys Thr Tyr Ala Asn Ser Val Gln Ala Tyr
210                 215                 220

Val His Val Lys Asp Val Ala Leu Ala His Val Leu Val Leu Glu Thr
225                 230                 235                 240

Pro Ser Ala Ser Gly Arg Tyr Leu Cys Ala Glu Ser Val Leu His Arg
               245                 250                 255

Gly Asp Val Val Glu Ile Leu Ala Lys Phe Phe Pro Glu Tyr Asn Val
           260                 265                 270

Pro Thr Lys Cys Ser Asp Glu Val Asn Pro Arg Val Lys Pro Tyr Lys
       275                 280                 285

Phe Ser Asn Gln Lys Leu Arg Asp Leu Gly Leu Glu Phe Thr Pro Val
290                 295                 300

Lys Gln Cys Leu Tyr Glu Thr Val Lys Ser Leu Gln Lys Gly His
305                 310                 315                 320

Leu Pro Val Pro Ser Pro Glu Asp Ser Val Arg Ile Gln Gly
               325                 330                 335
```

(2) INFORMATION FOR SEQ ID NO: 7:

(i) SEQUENCE CHARACTERISTICS:
        (A) LENGTH: 1376 base pairs (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 99..1112

(xi) SEQUENCE DESCRIPTION: SEQ ID NO: 7:

```
GAAAACACAC CTCCTCTCTT CTTTGTCTCT GTCTGTTCTC CACTTTCCCA GTCACCAAAC        60

TCGTATGCAT ATAATTACAT TTATCTAAAT ATAACAAC ATG CCT GTT GAT GCT          113
                                          Met Pro Val Asp Ala
                                          1               5

TCA TCA CTT TCA GGC CAA GGC CAA ACT ATC TGT GTC ACC GGG GGT GGT        161
Ser Ser Leu Ser Gly Gln Gly Gln Thr Ile Cys Val Thr Gly Gly Gly
                10              15              20

GGT TTC ATT GCT TCT TGG ATG GTT AAA CTT CTT TTA GAT AAA GGT TAC        209
Gly Phe Ile Ala Ser Trp Met Val Lys Leu Leu Leu Asp Lys Gly Tyr
            25              30              35

ACT GTT AGA GGA ACT GCG AGG AAC CCA GCT GAT CCC AAG AAT TCT CAT        257
Thr Val Arg Gly Thr Ala Arg Asn Pro Ala Asp Pro Lys Asn Ser His
        40              45              50

TTG AGG GAG CTT GAA GGA GCT GAA GAA AGA TTA ACT TTA TGC AAA GCT        305
Leu Arg Glu Leu Glu Gly Ala Glu Glu Arg Leu Thr Leu Cys Lys Ala
55              60              65

GAT CTT CTT GAT TAT GAG TCT CTT AAA GAG GGT ATT CAA GGG TGT GAT        353
Asp Leu Leu Asp Tyr Glu Ser Leu Lys Glu Gly Ile Gln Gly Cys Asp
70              75              80              85

GGT GTT TTC CAC ACT GCT TCT CCT GTC ACA GAT GAT CCG GAA GAA ATG        401
Gly Val Phe His Thr Ala Ser Pro Val Thr Asp Asp Pro Glu Glu Met
                90              95              100

GTG GAG CCA GCA GTG AAC GGG ACC AAA AAT GTG ATA ATT GCG GCG GCT        449
Val Glu Pro Ala Val Asn Gly Thr Lys Asn Val Ile Ile Ala Ala Ala
            105             110             115

GAG GCC AAA GTC CGA CGA GTG GTG TTC ACG TCA TCA ATT GGC GCT GTG        497
Glu Ala Lys Val Arg Arg Val Val Phe Thr Ser Ser Ile Gly Ala Val
        120             125             130

TAC ATG GAT CCC AAT AAG GGC CCA GAT GTT GTC ATT GAT GAG TCT TGC        545
Tyr Met Asp Pro Asn Lys Gly Pro Asp Val Val Ile Asp Glu Ser Cys
135             140             145

TGG AGT GAT CTT GAA TTC TGC AAG AAC ACC AAG AAT TGG TAT TGC TAT        593
Trp Ser Asp Leu Glu Phe Cys Lys Asn Thr Lys Asn Trp Tyr Cys Tyr
150             155             160             165

GGA AAG GCT GTG GCA GAA CAA GCT GCA TGG GAT ATG GCT AAG GAG AAA        641
Gly Lys Ala Val Ala Glu Gln Ala Ala Trp Asp Met Ala Lys Glu Lys
                170             175             180

GGG GTG GAC CTA GTG GTG GTT AAC CCA GTG CTG GTG CTT GGA CCA TTG        689
Gly Val Asp Leu Val Val Val Asn Pro Val Leu Val Leu Gly Pro Leu
            185             190             195

TTG CAG CCC ACT GTC AAT GCT AGC ATC ACT CAC ATC CTC AAG TAC CTC        737
Leu Gln Pro Thr Val Asn Ala Ser Ile Thr His Ile Leu Lys Tyr Leu
        200             205             210

ACC GGC TCA GCC AAG ACA TAT GCT AAC TCT GTT CAA GCT TAT GTG CAT        785
Thr Gly Ser Ala Lys Thr Tyr Ala Asn Ser Val Gln Ala Tyr Val His
215             220             225

GTT AGG GAT GTG GCA CTA GCC CAC ATT TTA GTC TTT GAG ACG CCT TCC        833
Val Arg Asp Val Ala Leu Ala His Ile Leu Val Phe Glu Thr Pro Ser
230             235             240             245

GCC TCC GGC CGT TAC CTT TGC TCT GAG AGC GTT CTC CAC CGT GGA GAG        881
```

```
Ala Ser Gly Arg Tyr Leu Cys Ser Glu Ser Val Leu His Arg Gly Glu
            250                 255                 260

GTG GTG GAA ATC CTT GCA AAG TTC TTC CCT GAG TAC CCC ATC CCT ACC      929
Val Val Glu Ile Leu Ala Lys Phe Phe Pro Glu Tyr Pro Ile Pro Thr
            265                 270                 275

AAG TGC TCA GAT GAG AAG AAC CCA AGA AAA CAA CCT TAC AAG TTC TCA      977
Lys Cys Ser Asp Glu Lys Asn Pro Arg Lys Gln Pro Tyr Lys Phe Ser
            280                 285                 290

AAC CAG AAG CTA AGG GAT CTG GGT TTC GAA TTC ACC CCA GTA AAG CAG     1025
Asn Gln Lys Leu Arg Asp Leu Gly Phe Glu Phe Thr Pro Val Lys Gln
        295                 300                 305

TGT CTG TAT GAA ACT GTT AAG AGT TTG CAG GAA AAG GGT CAC CTT CCA     1073
Cys Leu Tyr Glu Thr Val Lys Ser Leu Gln Glu Lys Gly His Leu Pro
310                 315                 320                 325

ATC CCA AAA CAA GCT GCA GAA GAG TCT TTG AAA ATT CAA TAAGGCCTCT     1122
Ile Pro Lys Gln Ala Ala Glu Glu Ser Leu Lys Ile Gln
                330                 335

TGGAACTATT TATTAGGATT GTTCCATACC CCAAGTTTGG ATCGCAAATG CTAGGGAA    1182

GAGCATATTA AAGAATGCCA ATGTGCAGGT GTTTTAGTAT TTTACATGAA GAACTCTG    1242

TATCCTTGTG CTTATAATAA TTTTTTTCAA GTGAGTGTCT TCAAATGTTC AACTTGTA    1302

TGTGGTTGTC TAACTTTATC CAGTTTCAAT ATAAAAGAGG AACGATTCTA TGTCTTAA    1362

AAAAAAAAAA AAAA                                                    1376

(2) INFORMATION FOR SEQ ID NO: 8:

(i) SEQUENCE CHARACTERISTICS:
        (A) LENGTH: 338 amino acids
        (B) TYPE: amino acid
        (D) TOPOLOGY: linear (ii) MOLECULE TYPE: protein (xi) SEQUENCE DESCRIPTION: SEQ ID NO: 8:

Met Pro Val Asp Ala Ser Ser Leu Ser Gly Gln Gly Gln Thr Ile Cys
 1               5                  10                  15

Val Thr Gly Gly Gly Gly Phe Ile Ala Ser Trp Met Val Lys Leu Leu
                20                  25                  30

Leu Asp Lys Gly Tyr Thr Val Arg Gly Thr Ala Arg Asn Pro Ala Asp
            35                  40                  45

Pro Lys Asn Ser His Leu Arg Glu Leu Glu Gly Ala Glu Glu Arg Leu
        50                  55                  60

Thr Leu Cys Lys Ala Asp Leu Leu Asp Tyr Glu Ser Leu Lys Glu Gly
65                  70                  75                  80

Ile Gln Gly Cys Asp Gly Val Phe His Thr Ala Ser Pro Val Thr Asp
                85                  90                  95

Asp Pro Glu Glu Met Val Glu Pro Ala Val Asn Gly Thr Lys Asn Val
            100                 105                 110

Ile Ile Ala Ala Ala Glu Ala Lys Val Arg Arg Val Phe Thr Ser
        115                 120                 125

Ser Ile Gly Ala Val Tyr Met Asp Pro Asn Lys Gly Pro Asp Val Val
    130                 135                 140

Ile Asp Glu Ser Cys Trp Ser Asp Leu Glu Phe Cys Lys Asn Thr Lys
145                 150                 155                 160

Asn Trp Tyr Cys Tyr Gly Lys Ala Val Ala Glu Gln Ala Ala Trp Asp
                165                 170                 175

Met Ala Lys Glu Lys Gly Val Asp Leu Val Val Val Asn Pro Val Leu
```

```
                      180                 185                 190
Val Leu Gly Pro Leu Leu Gln Pro Thr Val Asn Ala Ser Ile Thr His
            195                 200                 205

Ile Leu Lys Tyr Leu Thr Gly Ser Ala Lys Thr Tyr Ala Asn Ser Val
    210                 215                 220

Gln Ala Tyr Val His Val Arg Asp Val Ala Leu Ala His Ile Leu Val
225                 230                 235                 240

Phe Glu Thr Pro Ser Ala Ser Gly Arg Tyr Leu Cys Ser Glu Ser Val
                245                 250                 255

Leu His Arg Gly Glu Val Val Glu Ile Leu Ala Lys Phe Phe Pro Glu
            260                 265                 270

Tyr Pro Ile Pro Thr Lys Cys Ser Asp Glu Lys Asn Pro Arg Lys Gln
        275                 280                 285

Pro Tyr Lys Phe Ser Asn Gln Lys Leu Arg Asp Leu Gly Phe Glu Phe
    290                 295                 300

Thr Pro Val Lys Gln Cys Leu Tyr Glu Thr Val Lys Ser Leu Gln Glu
305                 310                 315                 320

Lys Gly His Leu Pro Ile Pro Lys Gln Ala Ala Glu Glu Ser Leu Lys
                325                 330                 335

Ile Gln (2) INFORMATION FOR SEQ ID NO: 9:

(i) SEQUENCE CHARACTERISTICS:
        (A) LENGTH: 1273 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 66..1091

(xi) SEQUENCE DESCRIPTION: SEQ ID NO: 9:

TCGTAGCTCT TCCCTTTCAC CAACAAGCTA GTTTAGACAA GTACAGTGGT ACTGTAAGAG       60

CAACA ATG ACC GTT GTC GAC GCC GCC GCG CCG CAG CTG CCT GGC CAT          107
      Met Thr Val Val Asp Ala Ala Ala Pro Gln Leu Pro Gly His
       1               5                  10

GGG CAG ACC GTG TGC GTC ACC GGC GCC GCG GGG TAC ATC GCG TCG GGG        155
Gly Gln Thr Val Cys Val Thr Gly Ala Ala Gly Tyr Ile Ala Ser Gly
 15                  20                  25                  30

CTC GTC AAG CTG CTC CTG GAG AGA GGC TAC ACC GTG AAG GGC ACA GTG        203
Leu Val Lys Leu Leu Leu Glu Arg Gly Tyr Thr Val Lys Gly Thr Val
                 35                  40                  45

AGG AAC CCA GAT GAT CCC AAG AAC GCC CAC CTG AAG GCG CTG GAC GGC        251
Arg Asn Pro Asp Asp Pro Lys Asn Ala His Leu Lys Ala Leu Asp Gly
             50                  55                  60

GCC ACC AAG AGG CTG ATC CTC TGC AAA GCC GAC CTC CTC GAC TAC GAC        299
Ala Thr Lys Arg Leu Ile Leu Cys Lys Ala Asp Leu Leu Asp Tyr Asp
         65                  70                  75

GCC ATA TGC GCC GCC GTC GAG GGC TGC CAC GGC GTG TTC CAC ACC GCC        347
Ala Ile Cys Ala Ala Val Glu Gly Cys His Gly Val Phe His Thr Ala
     80                  85                  90

TCT CCA GTC ACC GAT GAT CCT GAG CAG ATG GTG GAG CCG GCG GTG CGG        395
Ser Pro Val Thr Asp Asp Pro Glu Gln Met Val Glu Pro Ala Val Arg
 95                 100                 105                 110

GGC ACG GAG TAC GTG ATC AAC GCG GCA GCG GAT GCG GGA ACG GTG CGC        443
```

```
Gly Thr Glu Tyr Val Ile Asn Ala Ala Ala Asp Ala Gly Thr Val Arg
            115                 120                 125

CGG GTG GTG TTC ACG TCG TCA ATC GGT GCC ATC ACC ATG GAC CCC AAC      491
Arg Val Val Phe Thr Ser Ser Ile Gly Ala Ile Thr Met Asp Pro Asn
        130                 135                 140

CGC GGT CCT GAC GTA GTC GTC AAT GAG TCC TGC TGG AGC GAC CTC GAA      539
Arg Gly Pro Asp Val Val Val Asn Glu Ser Cys Trp Ser Asp Leu Glu
            145                 150                 155

TTC TGC AAG AAA ACC AAG AAC TGG TAC TGC TAC GGC AAG GCC GTG GCG      587
Phe Cys Lys Lys Thr Lys Asn Trp Tyr Cys Tyr Gly Lys Ala Val Ala
        160                 165                 170

GAG CAG GCT GCG TGG GAG GCG GCC AGG AAG CGC GGC ATC GAC CTC GTC      635
Glu Gln Ala Ala Trp Glu Ala Ala Arg Lys Arg Gly Ile Asp Leu Val
175                 180                 185                 190

GTC GTG AAC CCT GTG CTC GTG GTA GGG CCG CTG CTG CAA CCA ACG GTG      683
Val Val Asn Pro Val Leu Val Val Gly Pro Leu Leu Gln Pro Thr Val
                195                 200                 205

AAC GCT AGC GCC GCA CAC ATC CTC AAG TAC CTC GAC GGC TCG GCC AAG      731
Asn Ala Ser Ala Ala His Ile Leu Lys Tyr Leu Asp Gly Ser Ala Lys
            210                 215                 220

AAG TAC GCC AAC GCT GTG CAG TCA TAC GTA GAC GTG CGT GAC GTA GCC      779
Lys Tyr Ala Asn Ala Val Gln Ser Tyr Val Asp Val Arg Asp Val Ala
        225                 230                 235

GGC GCG CAC ATC CGG GTG TTC GAG GCG CCT GAG GCG TCG GGC CGG TAC      827
Gly Ala His Ile Arg Val Phe Glu Ala Pro Glu Ala Ser Gly Arg Tyr
240                 245                 250

CTC TGC GCC GAG CGC GTG CTG CAC CGT GGG GAC GTT GTC CAA ATC CTC      875
Leu Cys Ala Glu Arg Val Leu His Arg Gly Asp Val Val Gln Ile Leu
255                 260                 265                 270

AGC AAA CTC TTG CCT GAG TAC CCT GTG CCA ACA AGG TGC TCT GAT GAA      923
Ser Lys Leu Leu Pro Glu Tyr Pro Val Pro Thr Arg Cys Ser Asp Glu
                275                 280                 285

GTG AAC CCA CGG AAG CAG CCT TAT AAG ATG TCC AAC CAG AAG CTG CAG      971
Val Asn Pro Arg Lys Gln Pro Tyr Lys Met Ser Asn Gln Lys Leu Gln
            290                 295                 300

GAT CTT GGC CTC CAG TTC ACT CCT GTG AAC GAC TCT CTG TAT GAG ACC     1019
Asp Leu Gly Leu Gln Phe Thr Pro Val Asn Asp Ser Leu Tyr Glu Thr
        305                 310                 315

GTG AAG AGC CTC CAG GAG AAG GGA CAT CTC CTA GTA CCA AGC AAA CCC     1067
Val Lys Ser Leu Gln Glu Lys Gly His Leu Leu Val Pro Ser Lys Pro
320                 325                 330

GAG GGA TTA AAC GGT GTA ACG GCA TGATACTGCT AAGAAGCAG CAGAGTTCA      1121
Glu Gly Leu Asn Gly Val Thr Ala
335                 340

GTGCTCCTGT AACATGGTCA AACATGAGTT GTTTTTCTGT ATAAATTCTA TCCAGTAT     1181

TGTTATTTAA GTGAACTAAG AGAACAGAAT ATTGTATCAT CTTCGATGTC CAATACCT     1241

AAGTGATTTG TTTTGCCACC TAAAAAAAAA AA                                 1273

(2) INFORMATION FOR SEQ ID NO: 10:

(i) SEQUENCE CHARACTERISTICS:
        (A) LENGTH: 342 amino acids
        (B) TYPE: amino acid
        (D) TOPOLOGY: linear (ii) MOLECULE TYPE: protein (xi) SEQUENCE DESCRIPTION: SEQ ID NO: 10:

Met Thr Val Val Asp Ala Ala Ala Pro Gln Leu Pro Gly His Gly Gln
1               5                   10                  15
```

```
Thr Val Cys Val Thr Gly Ala Ala Gly Tyr Ile Ala Ser Gly Leu Val
             20                  25                  30

Lys Leu Leu Leu Glu Arg Gly Tyr Thr Val Lys Gly Thr Val Arg Asn
         35                  40                  45

Pro Asp Asp Pro Lys Asn Ala His Leu Lys Ala Leu Asp Gly Ala Thr
     50                  55                  60

Lys Arg Leu Ile Leu Cys Lys Ala Asp Leu Leu Asp Tyr Asp Ala Ile
 65                  70                  75                  80

Cys Ala Ala Val Glu Gly Cys His Gly Val Phe His Thr Ala Ser Pro
                 85                  90                  95

Val Thr Asp Asp Pro Glu Gln Met Val Glu Pro Ala Val Arg Gly Thr
            100                 105                 110

Glu Tyr Val Ile Asn Ala Ala Asp Ala Gly Thr Val Arg Arg Val
        115                 120                 125

Val Phe Thr Ser Ser Ile Gly Ala Ile Thr Met Asp Pro Asn Arg Gly
    130                 135                 140

Pro Asp Val Val Asn Glu Ser Cys Trp Ser Asp Leu Glu Phe Cys
145                 150                 155                 160

Lys Lys Thr Lys Asn Trp Tyr Cys Tyr Gly Lys Ala Val Ala Glu Gln
                165                 170                 175

Ala Ala Trp Glu Ala Ala Arg Lys Arg Gly Ile Asp Leu Val Val Val
            180                 185                 190

Asn Pro Val Leu Val Gly Pro Leu Leu Gln Pro Thr Val Asn Ala
        195                 200                 205

Ser Ala Ala His Ile Leu Lys Tyr Leu Asp Gly Ser Ala Lys Lys Tyr
    210                 215                 220

Ala Asn Ala Val Gln Ser Tyr Val Asp Val Arg Asp Val Ala Gly Ala
225                 230                 235                 240

His Ile Arg Val Phe Glu Ala Pro Glu Ala Ser Gly Arg Tyr Leu Cys
                245                 250                 255

Ala Glu Arg Val Leu His Arg Gly Asp Val Val Gln Ile Leu Ser Lys
            260                 265                 270

Leu Leu Pro Glu Tyr Pro Val Pro Thr Arg Cys Ser Asp Glu Val Asn
        275                 280                 285

Pro Arg Lys Gln Pro Tyr Lys Met Ser Asn Gln Lys Leu Gln Asp Leu
290                 295                 300

Gly Leu Gln Phe Thr Pro Val Asn Asp Ser Leu Tyr Glu Thr Val Lys
305                 310                 315                 320

Ser Leu Gln Glu Lys Gly His Leu Leu Val Pro Ser Lys Pro Glu Gly
                325                 330                 335

Leu Asn Gly Val Thr Ala
            340

(2) INFORMATION FOR SEQ ID NO: 11:

(i) SEQUENCE CHARACTERISTICS:
        (A) LENGTH: 1293 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 95..1108
```

-continued (xi) SEQUENCE DESCRIPTION: SEQ ID NO: 11:

```
CCGAGCCTAT TTCTTCCCTA TATCCACTCA TCCTTGTCTT ATATCATCAT CATCATCATC        60

TACCTAAACC TGAGCTCAAC AGAAAAGTAA TACC ATG CCG TCA GTT TCC GGC           112
                                     Met Pro Ser Val Ser Gly
                                      1               5

CAA ATC GTT TGT GTT ACT GGC GCC GGA GGT TTC ATC GCC TCT TGG CTC        160
Gln Ile Val Cys Val Thr Gly Ala Gly Gly Phe Ile Ala Ser Trp Leu
         10                  15                  20

GTT AAA ATT CTT CTG GAA AAA GGC TAC ACT GTT AGA GGA ACA GTA CGA        208
Val Lys Ile Leu Leu Glu Lys Gly Tyr Thr Val Arg Gly Thr Val Arg
     25                  30                  35

AAT CCA GAT GAT CGA AAA AAT AGT CAT TTG AGG GAG CTT GAA CGA GCA        256
Asn Pro Asp Asp Arg Lys Asn Ser His Leu Arg Glu Leu Glu Arg Ala
 40                  45                  50

AAA GAG ACA TTG ACT CTG TGC AGA GCT GAT CTT CTT GAT TTT CAG AGT        304
Lys Glu Thr Leu Thr Leu Cys Arg Ala Asp Leu Leu Asp Phe Gln Ser
 55                  60                  65                  70

TTG CGA GAA GCA ATC AGC GGC TGT GAC GGA GTT TTC CAC ACA CGT TCT        352
Leu Arg Glu Ala Ile Ser Gly Cys Asp Gly Val Phe His Thr Arg Ser
                 75                  80                  85

CCT GTC ACT GAT GAT CCA GAA CAA ATG GTG GAG CCA GCA GTT ATT GGT        400
Pro Val Thr Asp Asp Pro Glu Gln Met Val Glu Pro Ala Val Ile Gly
             90                  95                 100

ACA AAG AAT GTG ATA ACG GCA GCA GCA GAG GCC AAG GTG CGA CGT GTG        448
Thr Lys Asn Val Ile Thr Ala Ala Ala Glu Ala Lys Val Arg Arg Val
        105                 110                 115

GTG TTC ACT TCG TCA ATT GGT GCT GTG TAT ATG GAC CCA AAC AGG GAC        496
Val Phe Thr Ser Ser Ile Gly Ala Val Tyr Met Asp Pro Asn Arg Asp
    120                 125                 130

CCT GAT AAG GTT GTC GAC GAG ACT TGT TGG AGT GAT CCT GAC TTC TGC        544
Pro Asp Lys Val Val Asp Glu Thr Cys Trp Ser Asp Pro Asp Phe Cys
135                 140                 145                 150

AAA AAC ACC AAG AAT TGG TAT TGT TAT GGG AAG ATG GTG GCA GAA CAA        592
Lys Asn Thr Lys Asn Trp Tyr Cys Tyr Gly Lys Met Val Ala Glu Gln
                155                 160                 165

GCA GCA TGG GAC GAA GCA AGG GAG AAA GGA GTC GAT TTG GTG GCA ATC        640
Ala Ala Trp Asp Glu Ala Arg Glu Lys Gly Val Asp Leu Val Ala Ile
            170                 175                 180

AAC CCA GTG TTG GTG CTT GGA CCA CTG CTC CAA CAG AAT GTG AAT GCC        688
Asn Pro Val Leu Val Leu Gly Pro Leu Leu Gln Gln Asn Val Asn Ala
        185                 190                 195

AGT GTT CTT CAC ATC CAC AAG TAC CTA ACT GGC TCT GCT AAA ACA TAT        736
Ser Val Leu His Ile His Lys Tyr Leu Thr Gly Ser Ala Lys Thr Tyr
    200                 205                 210

ACG TCC AAT TCA CTT CAG GCA TAT GTT CAT GTT AGG GAT GTG GCT TTA        784
Thr Ser Asn Ser Leu Gln Ala Tyr Val His Val Arg Asp Val Ala Leu
215                 220                 225                 230

CGT CAC ATA CTT GTG TAC GAG ACA CCT TCT GCA TCT GGC CGT TAT CTC        832
Arg His Ile Leu Val Tyr Glu Thr Pro Ser Ala Ser Gly Arg Tyr Leu
                235                 240                 245

TGT GCC GAG AGT GTG CTG CAT CGC TGC GAT GTG GTT GAA ATT CTC GCC        880
Cys Ala Glu Ser Val Leu His Arg Cys Asp Val Val Glu Ile Leu Ala
            250                 255                 260

AAA TTC TTC CCG GAG TAT CCT ATC CCC ACC AAG TGT TCA GAT GTG ACG        928
Lys Phe Phe Pro Glu Tyr Pro Ile Pro Thr Lys Cys Ser Asp Val Thr
        265                 270                 275

AAG CCA AGG GTA AAA CCG TAC AAA TTC TCA AAC CAA AAG CTA AAG GAT        976
Lys Pro Arg Val Lys Pro Tyr Lys Phe Ser Asn Gln Lys Leu Lys Asp
    280                 285                 290
```

```
TTG GGT CTG GAG TTT ACA CCA GTA CAA TGC TTA TAT GAA ACG GTG AAG    1024
Leu Gly Leu Glu Phe Thr Pro Val Gln Cys Leu Tyr Glu Thr Val Lys
295                 300                 305                 310

AGT CTA CAA GAG AAA GGT CAC CTT CCA ATT CCT ACT CAA AAG GAT GAG    1072
Ser Leu Gln Glu Lys Gly His Leu Pro Ile Pro Thr Gln Lys Asp Glu
                315                 320                 325

ATT ATT CGA ATT CAG TCT GAG AAA TTC AGA AGC TCT TAGCATGTAT         1118
Ile Ile Arg Ile Gln Ser Glu Lys Phe Arg Ser Ser
                330                 335

TGAGGAAAAG GGATCAATGG TTAAAGTTGA CCATGGCGTT GTCCCTTTAT GTACCAAG    1178

CAAATGCACC TAGAAATTTA CTTGTCTACT CTGTTGTACT TTTACTTGTC ATGGAAAT    1238

TTTTAGTGTT TCATTGTTA TGAGATATAT TTTGGTGTAA AAAAAAAAAA AAAAA        1293

(2) INFORMATION FOR SEQ ID NO: 12:

(i) SEQUENCE CHARACTERISTICS:
        (A) LENGTH: 338 amino acids
        (B) TYPE: amino acid
        (D) TOPOLOGY: linear (ii) MOLECULE TYPE: protein (xi) SEQUENCE DESCRIPTION: SEQ ID NO: 12:

Met Pro Ser Val Ser Gly Gln Ile Val Cys Val Thr Gly Ala Gly Gly
1               5                   10                  15

Phe Ile Ala Ser Trp Leu Val Lys Ile Leu Leu Glu Lys Gly Tyr Thr
            20                  25                  30

Val Arg Gly Thr Val Arg Asn Pro Asp Asp Arg Lys Asn Ser His Leu
        35                  40                  45

Arg Glu Leu Glu Arg Ala Lys Glu Thr Leu Thr Leu Cys Arg Ala Asp
    50                  55                  60

Leu Leu Asp Phe Gln Ser Leu Arg Glu Ala Ile Ser Gly Cys Asp Gly
65                  70                  75                  80

Val Phe His Thr Arg Ser Pro Val Thr Asp Asp Pro Glu Gln Met Val
            85                  90                  95

Glu Pro Ala Val Ile Gly Thr Lys Asn Val Ile Thr Ala Ala Ala Glu
            100                 105                 110

Ala Lys Val Arg Arg Val Val Phe Thr Ser Ser Ile Gly Ala Val Tyr
        115                 120                 125

Met Asp Pro Asn Arg Asp Pro Asp Lys Val Val Asp Glu Thr Cys Trp
    130                 135                 140

Ser Asp Pro Asp Phe Cys Lys Asn Thr Lys Asn Trp Tyr Cys Tyr Gly
145                 150                 155                 160

Lys Met Val Ala Glu Gln Ala Ala Trp Asp Glu Ala Arg Glu Lys Gly
                165                 170                 175

Val Asp Leu Val Ala Ile Asn Pro Val Leu Val Leu Gly Pro Leu Leu
            180                 185                 190

Gln Gln Asn Val Asn Ala Ser Val Leu His Ile His Lys Tyr Leu Thr
        195                 200                 205

Gly Ser Ala Lys Thr Tyr Thr Ser Asn Ser Leu Gln Ala Tyr Val His
    210                 215                 220

Val Arg Asp Val Ala Leu Arg His Ile Leu Val Tyr Glu Thr Pro Ser
225                 230                 235                 240

Ala Ser Gly Arg Tyr Leu Cys Ala Glu Ser Val Leu His Arg Cys Asp
                245                 250                 255
```

```
Val Val Glu Ile Leu Ala Lys Phe Phe Pro Glu Tyr Pro Ile Pro Thr
            260                 265                 270

Lys Cys Ser Asp Val Thr Lys Pro Arg Val Lys Pro Tyr Lys Phe Ser
        275                 280                 285

Asn Gln Lys Leu Lys Asp Leu Gly Leu Glu Phe Thr Pro Val Gln Cys
    290                 295                 300

Leu Tyr Glu Thr Val Lys Ser Leu Gln Glu Lys Gly His Leu Pro Ile
305                 310                 315                 320

Pro Thr Gln Lys Asp Glu Ile Ile Arg Ile Gln Ser Glu Lys Phe Arg
                325                 330                 335

Ser Ser (2) INFORMATION FOR SEQ ID NO: 13:

(i) SEQUENCE CHARACTERISTICS:
        (A) LENGTH: 1297 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 136..1140

(xi) SEQUENCE DESCRIPTION: SEQ ID NO: 13:
```

| | |
|---|---:|
| CGGCCGGGAC GACCCGTTCC TCTTCTTCCG GGTCACCGTC ACCATGTTAC ACAACATCTC | 60 |
| CGGCTAAAAA AAAAAGGAAA AAAAGCGCAA CCTCCACCTC CTGAACCCCT CTCCCCCCT | 120 |

```
GCCGGCAATC CCACC ATG CCC GTC GAC GCC CTC CCC GGT TCC GGC CAG ACC    171
                 Met Pro Val Asp Ala Leu Pro Gly Ser Gly Gln Thr
                  1               5                  10

GTC TGC GTC ACC GGC GCC GGC GGG TTC ATC GCC TCC TGG ATT GTC AAG    219
Val Cys Val Thr Gly Ala Gly Gly Phe Ile Ala Ser Trp Ile Val Lys
         15                  20                  25

CTT CTC CTC GAG CGA GGC TAC ACC GTG CGA GGA ACC GTC AGG AAC CCA    267
Leu Leu Leu Glu Arg Gly Tyr Thr Val Arg Gly Thr Val Arg Asn Pro
     30                  35                  40

GAC GAC CCG AAG AAT GGT CAT CTG AGA GAT CTG GAA GGA GCC AGC GAG    315
Asp Asp Pro Lys Asn Gly His Leu Arg Asp Leu Glu Gly Ala Ser Glu
 45                  50                  55                  60

AGG CTG ACG CTG TAC AAG GGT GAT CTG ATG GAC GAC GGG AGC TTG GAA    363
Arg Leu Thr Leu Tyr Lys Gly Asp Leu Met Asp Asp Gly Ser Leu Glu
                 65                  70                  75

GAA GCC ATC AAG GGG TGC GAC GGC GTC GTC CAC ACC GCC TCT CCG GTC    411
Glu Ala Ile Lys Gly Cys Asp Gly Val Val His Thr Ala Ser Pro Val
             80                  85                  90

ACC GAC GAT CCT GAG CAA ATG GTG GAG CCA GCG GTG ATC GGG ACG AAA    459
Thr Asp Asp Pro Glu Gln Met Val Glu Pro Ala Val Ile Gly Thr Lys
         95                  100                 105

AAT GTG ATC GTC GCA GCG GCG GAG GCC AAG GTC CGG CGG GTT GTG TTC    507
Asn Val Ile Val Ala Ala Ala Glu Ala Lys Val Arg Arg Val Val Phe
     110                 115                 120

ACC TCC TCC ATC GGT GCA GTC ACC ATG GAC CCC AAC CGG GCA GAC GTT    555
Thr Ser Ser Ile Gly Ala Val Thr Met Asp Pro Asn Arg Ala Asp Val
125                 130                 135                 140

GTG GTG GAC GAG TCT TGT TGG AGC GAC CTC GAA TTT TGC AAG AGC ACT    603
Val Val Asp Glu Ser Cys Trp Ser Asp Leu Glu Phe Cys Lys Ser Thr
                145                 150                 155

AAG AAC TGG TAT TGC TAC GGC AAG GCA GTG GCG GAG AAG GCC GCT TGG    651
```

```
                                                                         -continued Lys Asn Trp Tyr Cys Tyr Gly Lys Ala Val Ala Glu Lys Ala Ala Trp
        160                 165                 170

CCA GAG GGC AAG GAG AGA GGG GTT GAC CTC GTG GTG ATT AAC CCT GTG              699
Pro Glu Gly Lys Glu Arg Gly Val Asp Leu Val Val Ile Asn Pro Val
            175                 180                 185

CTC GTG CTT GGA CCG CTC CTT CAG TCG ACG ATC AAT GCG AGC ATC ATC              747
Leu Val Leu Gly Pro Leu Leu Gln Ser Thr Ile Asn Ala Ser Ile Ile
        190                 195                 200

CAC ATC CTC AAG TAC TTG ACT GGC TCA GCC AAG ACC TAC GCC AAC TCG              795
His Ile Leu Lys Tyr Leu Thr Gly Ser Ala Lys Thr Tyr Ala Asn Ser
205                 210                 215                 220

GTC CAG GCG TAC GTG CAC GTC AAG GAC GTC GCG CTT GCC CAC GTC CTT              843
Val Gln Ala Tyr Val His Val Lys Asp Val Ala Leu Ala His Val Leu
                225                 230                 235

GTC TTG GAG ACC CCA TCC GCC TCA GGC CGC TAT TTG TGC GCC GAG AGC              891
Val Leu Glu Thr Pro Ser Ala Ser Gly Arg Tyr Leu Cys Ala Glu Ser
            240                 245                 250

GTC CTC CAC CGT GGC GAT GTG GTG GAA ATC CTT GCC AAG TTC TTC CCT              939
Val Leu His Arg Gly Asp Val Val Glu Ile Leu Ala Lys Phe Phe Pro
        255                 260                 265

GAG TAT AAT GTA CCG ACC AAG TGC TCT GAT GAG GTG AAC CCA AGA GTA              987
Glu Tyr Asn Val Pro Thr Lys Cys Ser Asp Glu Val Asn Pro Arg Val
270                 275                 280

AAA CCA TAC AAG TTC TCC AAC CAG AAG CTG AGA GAC TTG GGG CTC GAG             1035
Lys Pro Tyr Lys Phe Ser Asn Gln Lys Leu Arg Asp Leu Gly Leu Glu
285                 290                 295                 300

TTC ACC CCG GTG AAG CAG TGC CTG TAC GAA ACT GTC AAG AGC TTG CAG             1083
Phe Thr Pro Val Lys Gln Cys Leu Tyr Glu Thr Val Lys Ser Leu Gln
                305                 310                 315

GAG AAA GGC CAC CTA CCA GTC CCC TCC CCG CCG GAA GAT TCG GTG CGT             1131
Glu Lys Gly His Leu Pro Val Pro Ser Pro Pro Glu Asp Ser Val Arg
            320                 325                 330

ATT CAG GGA TGATCTTAGA TCCATCACGG TGCGCATTTG TAATCCGGAG                     1180
Ile Gln Gly
        335

AAATGAGAGA AACATGTGGG AATTTGTTTG TACTTTTCTA AGTCAAACCT GGAGATAC             1240

ACCCTGAGTT CTGCATTGGA ATGGAAGTTG TCAATTGTTC CAAAAAAAAA AAAAAAA              1297

(2) INFORMATION FOR SEQ ID NO: 14:

(i) SEQUENCE CHARACTERISTICS:
        (A) LENGTH: 335 amino acids
        (B) TYPE: amino acid
        (D) TOPOLOGY: linear (ii) MOLECULE TYPE: protein (xi) SEQUENCE DESCRIPTION: SEQ ID NO: 14:

Met Pro Val Asp Ala Leu Pro Gly Ser Gly Gln Thr Val Cys Val Thr
  1               5                  10                  15

Gly Ala Gly Gly Phe Ile Ala Ser Trp Ile Val Lys Leu Leu Leu Glu
                20                  25                  30

Arg Gly Tyr Thr Val Arg Gly Thr Val Arg Asn Pro Asp Asp Pro Lys
            35                  40                  45

Asn Gly His Leu Arg Asp Leu Glu Gly Ala Ser Glu Arg Leu Thr Leu
        50                  55                  60

Tyr Lys Gly Asp Leu Met Asp Asp Gly Ser Leu Glu Glu Ala Ile Lys
 65                  70                  75                  80

Gly Cys Asp Gly Val Val His Thr Ala Ser Pro Val Thr Asp Asp Pro
```

-continued

```
                    85                  90                  95
Glu Gln Met Val Glu Pro Ala Val Ile Gly Thr Lys Asn Val Ile Val
                100                 105                 110
Ala Ala Ala Glu Ala Lys Val Arg Arg Val Val Phe Thr Ser Ser Ile
            115                 120                 125
Gly Ala Val Thr Met Asp Pro Asn Arg Ala Asp Val Val Asp Glu
    130                 135                 140
Ser Cys Trp Ser Asp Leu Glu Phe Cys Lys Ser Thr Lys Asn Trp Tyr
145                 150                 155                 160
Cys Tyr Gly Lys Ala Val Ala Glu Lys Ala Ala Trp Pro Glu Gly Lys
                165                 170                 175
Glu Arg Gly Val Asp Leu Val Val Ile Asn Pro Val Leu Val Leu Gly
            180                 185                 190
Pro Leu Leu Gln Ser Thr Ile Asn Ala Ser Ile Ile His Ile Leu Lys
        195                 200                 205
Tyr Leu Thr Gly Ser Ala Lys Thr Tyr Ala Asn Ser Val Gln Ala Tyr
    210                 215                 220
Val His Val Lys Asp Val Ala Leu Ala His Val Leu Val Leu Glu Thr
225                 230                 235                 240
Pro Ser Ala Ser Gly Arg Tyr Leu Cys Ala Glu Ser Val Leu His Arg
                245                 250                 255
Gly Asp Val Val Glu Ile Leu Ala Lys Phe Phe Pro Glu Tyr Asn Val
            260                 265                 270
Pro Thr Lys Cys Ser Asp Glu Val Asn Pro Arg Val Lys Pro Tyr Lys
        275                 280                 285
Phe Ser Asn Gln Lys Leu Arg Asp Leu Gly Leu Glu Phe Thr Pro Val
    290                 295                 300
Lys Gln Cys Leu Tyr Glu Thr Val Lys Ser Leu Gln Glu Lys Gly His
305                 310                 315                 320
Leu Pro Val Pro Ser Pro Glu Asp Ser Val Arg Ile Gln Gly
                325                 330                 335
```

(2) INFORMATION FOR SEQ ID NO: 15:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 15:

```
Asn Trp Tyr Cys Tyr Gly Lys
1               5
```

(2) INFORMATION FOR SEQ ID NO: 16:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /label= Xaa
           /note= "any amino acid"

(xi) SEQUENCE DESCRIPTION: SEQ ID NO: 16:

His Leu Pro Val Pro Xaa Pro Pro Glu Asp Ser Val Arg
1               5                  10

(2) INFORMATION FOR SEQ ID NO: 17:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

Thr Tyr Ala Asn Ser Val Gln Ala Tyr Val His Val Lys
1               5                  10

(2) INFORMATION FOR SEQ ID NO: 18:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 18:

Gly Cys Asp Gly Val Val His Thr Ala Ser Pro Val Thr Asp Asp
1               5                  10                  15

(2) INFORMATION FOR SEQ ID NO: 19:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 19:

Leu Arg Asp Leu Gly Leu Glu Phe Thr Pro Val Lys
1               5                  10

(2) INFORMATION FOR SEQ ID NO: 20:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

Gly Asp Leu Met Asp Tyr Gly Ser Leu Glu Glu Ala Ile Lys
1               5                  10

(2) INFORMATION FOR SEQ ID NO: 21:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

Lys Asn Trp Tyr Cys Tyr Gly Lys
1               5

(2) INFORMATION FOR SEQ ID NO: 22:

(i) SEQUENCE CHARACTERISTICS:
            (A) LENGTH: 22 base pairs
            (B) TYPE: nucleic acid
            (C) STRANDEDNESS: both
            (D) TOPOLOGY: linear (ii) MOLECULE TYPE: cDNA (xi) SEQUENCE DESCRIPTION: SEQ ID NO: 22:

AARAAYTGGT AYTGYTAYGG AA                                             22

(2) INFORMATION FOR SEQ ID NO: 23:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 23:

Lys Gly Cys Asp Gly Val Val His Thr Ala Ser Pro Val Thr Asp As
1               5                   10                  15

(2) INFORMATION FOR SEQ ID NO: 24:

(i) SEQUENCE CHARACTERISTICS:
            (A) LENGTH: 19 base pairs
            (B) TYPE: nucleic acid
            (C) STRANDEDNESS: both
            (D) TOPOLOGY: linear (ii) MOLECULE TYPE: cDNA (xi) SEQUENCE DESCRIPTION: SEQ ID NO: 24:

AARGGTGYGA YGGGTGTCA                                                 19

(2) INFORMATION FOR SEQ ID NO: 25:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 25:

Lys Leu Arg Asp Leu Gly Leu Glu Phe Thr Pro Val Lys
1               5                   10

(2) INFORMATION FOR SEQ ID NO: 26:

(i) SEQUENCE CHARACTERISTICS:
            (A) LENGTH: 14 base pairs
            (B) TYPE: nucleic acid
            (C) STRANDEDNESS: both
            (D) TOPOLOGY: linear (ii) MOLECULE TYPE: cDNA -continued (xi) SEQUENCE DESCRIPTION: SEQ ID NO: 26:

GARTTYACCC GTAA                                                                    14

(2) INFORMATION FOR SEQ ID NO: 27:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 27:

Lys Gly Asp Leu Met Asp Tyr Gly Ser Leu Glu Glu Ala Ile Lys
1               5                   10                  15

(2) INFORMATION FOR SEQ ID NO: 28:

(i) SEQUENCE CHARACTERISTICS:
        (A) LENGTH: 21 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO: 28:

AARGGGAYYT ATGGAYTAYG G                                                            21

(2) INFORMATION FOR SEQ ID NO: 29:

(i) SEQUENCE CHARACTERISTICS:
        (A) LENGTH: 26 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO: 29:

GGCAATCCCC ATATGCCCGT CGACGC                                                       26

DNA SEQUENCES CODING FOR A CINNAMOYL COA REDUCTASE, AND APPLICATIONS THEREOF IN THE CONTROL OF LIGNIN CONTENTS IN PLANTS

The present invention relates to the use of DNA sequences which code for a cinnamoyl-CoA reductase (CCR) in plants, or any fragment of these sequences, or also any sequence derived from the latter, or their complementary sequences, in the context of carrying out processes for regulating the level of lignin in plants.

Lignin is a complex heterogeneous aromatic polymer which renders impermeable and reinforces the walls of certain plants cells.

Lignin is formed by polymerization of free radicals derived from monolignols, such as paracoumaryl, coniferyl and sinapyl alcohols (Higuchi, 1985, in Biosynthesis and degradation of wood components (T. Higuchi, ed.), Academic Press, Orlando, Fla. pp. 141–160).

Lignins have a wide variation in their relative content of monolignols, as a function of the species and the various tissues within the same plant This variation is probably caused and controlled by different activities and specificities of substrates, the enzymes necessary for biosynthesis of lignin monomers (Higuchi, 1985, loc. cit.).

Beyond its role in the structure and development of plants, lignin represents a major component of the terrestrial biomass and assumes a major economic and ecological significance (Brown, 1985, J. Appl. Biochem. 7, 371–387; Whetten and Sederoff, 1991, 1 orest Ecology and Management, 43, 301–316).

At the level of exploitation of the biomass, it is appropriate first to note that lignin is a limiting factor of the digestibility and nutritional yield of fodder plants. In fact, it is clearly demonstrated that the digestibility of fodder plants by ruminants is inversely proportional to the content of lignin in these plants, the nature of the lignins also being a determining factor in this phenomenon (Buxton and Roussel, 1988, Crop. Sci., 28, 553–558; Jung and Vogel, 1986, J. Anim., Sci., 62, 1703–1712).

Among the main fodder plants in which it would be of interest to reduce the lignin contents there may be mentioned: lucerne, fescue, maize, fodder used for silaging . . . .

It should also be noted that high lignin contents are partly responsible for the limited quality of sunflower cake intended for feeding cattle, and for the reduction in germinative capacities of certain seeds in the horticultural sector.

It may also be emphasized that the intense lignification which results during preservation of plant components after harvesting rapidly renders products such as asparagus, yam, carrots etc . . . unfit for consumption.

Furthermore, it is also appropriate to note that more than 50 million tonnes of lignin are extracted from ligneous material each year in the context of production of paper pulp in the paper industry. This extraction operation, which is necessary to obtain cellulose, is costly in energy and, secondly, causes pollution through the chemical compounds used for the extraction, which are found in the environment (Dean and Eriksson, 1992, Holzforschung, 46, 135–147: Whetten and Sederoff, 1991, loc. cit.).

To reduce the proportions of lignins (which make up to 20 to 30% of the dry matter, depending on the species) to a few per cent (2 to 5%) would represent an increase in yield and a substantial saving (chemical products), and would contribute to improving the environment (reduction in pollution). Given the scale of use of ligneous material, these decreases would have extremely significant repercussions. In this case, the species concerned could be poplar, eucalyptus, *Acacia magnium*, the genus Casuarina and all the angiosperms and gymnosperms used for the production of paper pulp.

It is clear that in the two sectors under consideration, the reduction in the levels of lignins must be moderated to preserve the characteristics of rigidity and the normal architecture of the plant (or the tree), since the lignins which strengthen the cell walls play a significant role in maintaining the erect habit of plants.

The natural variations in the lignin contents observed in nature for the same species (deviations which can be up to 6–8% of the dry matter among individuals) justify the reductions suggested above.

The resistance to degradation of lignin, like the difficulties encountered in the context of its extraction, are probably due to the complex structure of this polymer, which is made up of ether bonds and carbon-carbon bonds between the monomers, as well as to the numerous chemical bonds which exist between the lignin and the other components of the cell wall (Sarkanen and Ludwig, 1971, in Lignins: Occurrence, Formation, Structure and Reactions (K. V. Sarkanen and C. H. Kudwig ed.) New York: Wiley—Interscience, pp. 1–18).

Starting from cinnamoyl-CoA, the biosynthesis of lignins in plants is effected in the following manner:

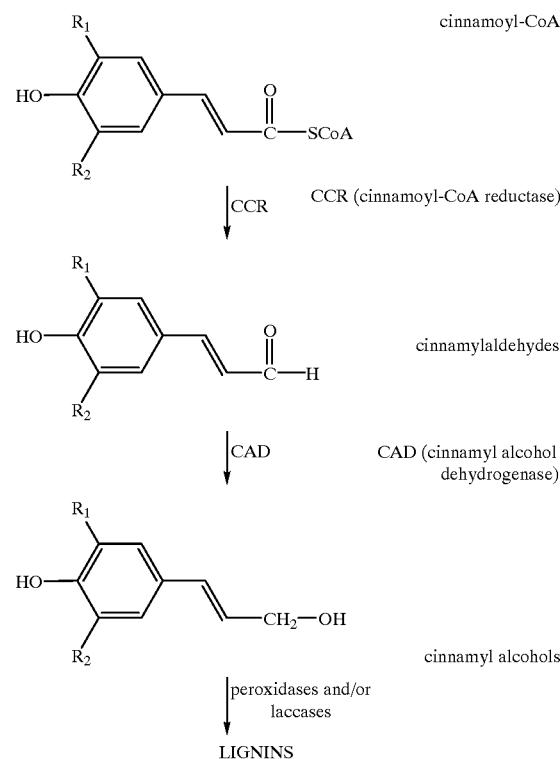

An approach to attempt to reduce the level of lignins in plants by genetic engineering would consist of inhibiting the synthesis of one of the enzymes in the biosynthesis chain of these lignins indicated above.

A particularly suitable technique in the context of such an approach is to use antisense mRNA which is capable of hybridizing with the mRNA which codes for these enzymes, and consequently to prevent, at least partly, the production of these enzymes from their corresponding mRNA.

Such an antisense strategy carried out with the aid of the gene which codes for the CAD in tobacco was the subject matter of European Patent Application no. 584 117, which describes the use of antisense mRNA which is capable of inhibiting the production of lignins in plants by hybridizing with the mRNA which codes for the CAD in these plants.

The results in the plants transformed in this way demonstrate a reduction in the activity of the CAD, but paradoxically the contents of lignins show no change. Complementary studies indicate that the lignins of transformed plants are different from control lignins, since the cinnamylaldehydes are incorporated directly into the lignin polymer.

One of the aims of the present invention is specifically that of providing a process which allows effective regulation of the contents of lignins in plants, either in the sense of a considerable reduction in these contents with respect to the normal contents in plants, or in the sense of an increase in these contents.

Another aim of the present invention is to provide tools for carrying out such a process, and more particularly constructions which can be used for the transformation of plants.

Another aim of the present invention is to provide genetically transformed plants, in particular fodder plants which can be digested better than non-transformed plants, or also transformed plants or trees for the production of paper pulp, from which the extraction of lignins would be facilitated and less polluting than in the case of non-transformed trees.

Another aim of the present invention is that of providing transformed plants which are more resistant to attacks from the environment, in particular to parasitic attacks, than the non-transformed plants are, or also transformed plants of a larger size, or of a smaller size (than that of the non-transformed plants).

The present invention relates to the use of recombinant nucleotide sequences containing one (or more) coding region(s), this (these) coding region(s) being made up of a nucleotide sequence chosen from the following:

the nucleotide sequence represented by SEQ ID NO 1 which codes for an mRNA, this mRNA itself coding for the cinnamoyl-CoA reductase (CCR) of lucerne represented by SEQ ID NO 2, the nucleotide sequence represented by SEQ ID NO 3 which codes for an mRNA, this mRNA itself coding for the CCR of maize represented by SEQ ID NO 4, a fragment of the nucleotide sequence represented by SEQ ID NO 1, or of that represented by SEQ ID NO 3, this fragment coding for a fragment of the CCR represented by SEQ ID NO 2 or for a fragment of the CCR represented by SEQ ID NO 3 respectively, this CCR fragment having an enzymatic activity equivalent to that of the two abovementioned CCRs, the nucleotide sequence complementary to that represented by SEQ ID NO 1 or SEQ ID NO 3, this complementary sequence coding for an antisense mRNA which is capable of hybridizing with the mRNA coded by the sequences SEQ ID NO 1 and SEQ ID NO 3 respectively, a fragment of the nucleotide sequence complementary to that represented by SEQ ID NO 1 or SEQ ID NO 3, this sequence fragment coding for an antisense mRNA which is capable of hybridizing with the mRNA which itself codes for the CCR represented by SEQ ID NO 2, or with the mRNA which itself codes for the CCR represented by SEQ ID NO 4 respectively, the nucleotide sequence derived from the sequence represented by SEQ ID NO 1 or SEQ ID NO 3, in particular by mutation and/or addition and/or suppression and/or substitution of one or more nucleotides, this derived sequence coding either for an mRNA which itself codes for the CCR represented by SEQ ID NO 2 or SEQ ID NO 4 respectively, or for a fragment or a protein derived from the latter, this fragment or derived protein having an enzymatic activity equivalent to that of the said CCRs in plants, the nucleotide sequence derived from the abovementioned complementary nucleotide sequence, or from the fragment of this complementary sequence as is described above, by mutation and/or addition and/or suppression and/or substitution of one or more nucleotides, this derived sequence coding for an antisense mRNA which is capable of hybridizing with one of the abovementioned mRNAs, for transformation of plant cells in order to obtain transgenic plants within which the biosynthesis of lignins is regulated either in the sense of an increase or in the sense of a reduction in the contents of lignins produced, with respect to the normal contents of lignins produced in the plants, and/or in the sense of a modification of the composition of the lignins produced by the said transgenic plants with respect to the lignins produced in the non-transformed plants, in particular by carrying out one of the processes, described below, for regulation of the amount of lignin in the plants.

"Derived nucleotide sequence" in the text above and below is understood as meaning any sequence having at least about 50% (preferably at least 70%) of nucleotides homologous to those of the sequence from which it is derived.

"Derived protein" in the text above and below is understood as meaning any protein having at least about 50% (preferably at least 70%) of amino acids homologous to those of the protein from which it is derived.

The present invention more particularly relates to any DNA sequence, characterized in that it comprises, as the coding region:

the nucleotide sequence represented by SEQ ID NO 1 which codes for an mRNA, this mRNA itself coding for the CCR represented by SEQ ID NO 2, or a fragment of the abovementioned nucleotide sequence, this fragment coding for a fragment of the CCR represented by SEQ ID NO 2) NO 2, this CCR fragment having an enzymatic activity equivalent to that of the abovementioned CCR, or any nucleotide sequence derived from the abovementioned sequence represented by SEQ ID NO 1, or from a fragment, as is described above, of this sequence, in particular by mutation and/or addition and/or suppression and/or substitution of one or more nucleotides, this derived sequence coding for an mRNA which itself codes for the CCR represented by SEQ ID NO 2, or for a protein derived from the latter and having an enzymatic activity equivalent to that of the said CCR in plants.

The present invention more particularly relates to any DNA sequence, characterized in that it contains, as the coding region:

the nucleotide sequence represented by SEQ ID NO 3 which codes for mRNA, this mRNA itself coding for the CCR represented by SEQ ID NO 4, or a fragment of the abovementioned nucleotide sequence, this fragment coding for a fragment of the CCR represented by SEQ ID NO 4, this CCR fragment having an enzymatic activity equivalent to that of the abovementioned CCR, or any nucleotide sequence derived from the abovementioned sequence represented by SEQ ID NO 3, or from a fragment, as is described above, of this sequence, in particular by mutation and/or addition and/or suppression and/or substitution of one or more nucleotides, this derived sequence coding for an mRNA which itself codes for the CCR represented by SEQ ID NO 4, or for a protein derived from the latter and having an enzymatic activity equivalent to that of the said CCR in plants.

Protein having an enzymatic activity equivalent to that of the CCRs present in plants, and more particularly the CCRs represented by SEQ ID NO 2 and SEQ ID NO 4, is understood as meaning any protein which possesses a CCR activity as measured by the method of Luderitz and Grisebach published in Eur. J. Biochem. (1981), 119:115–127.

By way of illustration, this method is carried out by spectrophotometric measurement of the reducing activity of the protein (CCR or derived) by monitoring the disappearance of the cinnamoyl-CoAs at 366 nm. The reaction takes place at 30° C. in the course of 2 to 10 minutes. The composition of the reaction medium is as follows: phosphate buffer 100 mM, pH 6.25, 0.1 mM NADPH, 70 $\mu$M feruloyl-CoA, 5 to 100 $\mu$l enzymatic extract in a total volume of 500 $\mu$l.

The invention also relates to any DNA sequence, characterized in that it contains, as the coding region:

the nucleotide sequence complementary to that represented by SEQ ID NO 1, this complementary sequence coding for an antisense mRNA which is capable of hybridizing with the mRNA which itself codes for the CCR represented by SEQ ID NO 2, that is to say the mRNA coded by the sequence represented by SEQ ID NO 1, or coded by a sequence derived from the latter, as is defined above, or a fragment of the abovementioned complementary sequence, this sequence fragment coding for an antisense mRNA which is capable of hybridizing with the mRNA which itself codes for the CCR represented by SEQ ID NO 2, as is defined above, or any nucleotide sequence derived from the abovementioned complementary sequence, or from the fragment of this complementary sequence as is described above, in particular by mutation and/or addition and/or suppression and/or substitution of one or more nucleotides, this derived sequence coding for an antisense mRNA which is capable of hybridizing with the abovementioned mRNA.

The present invention more particularly relates to any DNA sequence, characterized in that it contains, as the coding region:

the nucleotide sequence complementary to that represented by SEQ ID NO 3, this complementary sequence coding for an antisense mRNA which is capable of hybridizing with the mRNA which itself codes for the CCR represented by SEQ ID NO 4, that is to say the mRNA coded by the sequence represented by SEQ ID NO 3, or coded by a sequence derived from the latter, as is defined above, or a fragment of the abovementioned complementary sequence, this sequence fragment coding for an antisense mRNA which is capable of hybridizing with the mRNA which itself codes for the CCR represented by SEQ ID NO 4, as is defined above, or any nucleotide sequence derived from the abovementioned complementary sequence, or from the fragment of this complementary sequence as is described above, in particular by mutation and/or addition and/or suppression and/or substitution of one or more nucleotides, this derived sequence coding for an antisense mRNA which is capable of hybridizing with the abovementioned mRNA.

It goes without saying that the sequences represented by SEQ ID NO 1 and SEQ ID NO 3, the complementary sequences, the derived sequences and the sequence fragments of the invention which are mentioned above must be considered as being represented in the sense 5'→3'.

The first nucleotide of a complementary sequence in the sense 5'→3' as is described above is thus the complement of the last nucleotide of the sequence in the sense 5'→3' which codes for a CCR (or CCR fragment or derived protein), the second nucleotide of this complementary sequence is the complement of the last-but-one nucleotide of the sequence which codes for a CCR, and so on, up to the last nucleotide of the said complementary sequence, which is the complement of the first nucleotide of the sequence which codes for a CCR.

The mRNA coded by the abovementioned complementary sequence is such that, if this mRNA is represented in the sense 5'→3', its first nucleotide corresponds to the last nucleotide of the sequence which codes for a CCR, and thus hybridizes with the last nucleotide of the mRNA coded by the latter, while its last nucleotide corresponds to the first nucleotide of the sequence which codes for a CCR, and thus hybridizes with the first nucleotide of the mRNA coded by the latter.

Antisense mRNA in the text above and below is therefore understood as meaning any RNA coded by the said complementary sequence and represented in the reverse sense (3'→5') to the sense in which the mRNA coded by the sequence which codes for a CCR (or CCR fragment or derived protein) is represented, the latter mRNA being also called sense mRNA (5'→3').

The term antisense RNA therefore relates to an RNA sequence complementary to the sequence of bases of the messenger RNA, the term complementary being understood in the sense that each base (or a majority of the bases) of the antisense sequence (read in the sense 3'→5') is capable of pairing with the corresponding bases (G with C, A with U) of the messenger RNA (sequence read in the sense (5'→3').

The strategy of antisense RNAs in the context of the present invention is a molecular approach which is particularly suitable for the aim of modulation of the levels of lignins in plants. The antisense RNA is an RNA produced by transcription of the non-coding DNA strand (non-sense strand).

This antisense strategy is more particularly described in European Patent no. 240 208.

It is thought that the inhibition of the synthesis of a protein by the antisense strategy, under the circumstances the CCR in the present case, is the consequence of the formation of a duplex between the two complementary RNAs (sense and antisense), thus preventing the production of the protein. The mechanism remains obscure, however. The RNA-RNA complex can interfere either with a subsequent transcription, or with the maturation, transportation or translation, or even lead to a degradation of the mRNA.

A combination of these effects is also possible.

The invention also relates to any mRNA coded by a DNA sequence according to the invention, and more particularly:

the mRNA coded by the DNA sequence represented by SEQ ID NO 1, or coded by a fragment or a derived sequence, as are defined above, the said mRNA being capable of coding in its turn for the CCR present in lucerne, such as is represented by SEQ ID NO 2, or for a fragment of this CCR or a derived protein, as are defined above, the mRNA coded by the DNA sequence represented by SEQ ID NO 3, or coded by a fragment or a derived sequence, as are defined above, the said mRNA being capable of coding in its turn for the CCR present in maize, such as is represented by SEQ ID NO 4, or for a fragment of this CCR or a derived protein, as are defined above.

The invention also relates to any antisense mRNA as defined above, characterized in that it contains nucleotides complementary to all or only part of the nucleotides which make up an mRNA as described above according to the invention, the said antisense mRNA being capable of hybridizing (or of pairing) with the latter.

In this respect, the invention more particularly relates to the antisense mRNAs coded by the DNA sequences according to the invention, containing at least one region of 50 bases homologous to those of a region of the complementary sequences of the abovementioned DNA sequences of the invention.

There is no upper limit to the size of the DNA sequences which code for an antisense RNA according to the invention; they can be as long as the messenger usually produced in cells, or indeed as long as the genomic DNA sequence which codes for the mRNA of the CCR.

Such DNA sequences which code for an antisense RNA according to the invention advantageously contain between about 100 and about 1,000 base pairs.

The invention more particularly relates to any antisense sequence containing one (or more) antisense mRNA(s) as described above, or fragment(s) of this (these) antisense mRNA(s), and one (or more) sequence(s) corresponding to one (or more) catalytic domain(s) of a ribozyme.

In this respect, the invention more particularly relates to any antisense sequence as is described above containing the catalytic domain of a ribozyme flanked on both sides by arms of about 8 bases complementary to sequences which border a motif GUX (X representing C, U or A) contained in one of the mRNAs of the invention described above (also called target RNAs) (Haseloff J., et Gerlach W. L., 1988, Nature, 334:585–591).

The invention also relates to any DNA sequence which is capable of coding for an antisense sequence as is described above containing at least one catalytic domain of a ribozyme bonded to one or more antisense mRNA(s) of the invention, or fragment(s) of the antisense mRNA (advantageously fragments of about 8 bases as are described above).

The invention more particularly relates to:

any antisense mRNA as is described above, characterized in that it is coded by the nucleotide sequence complementary to that represented by SEQ ID NO 1, the said antisense mRNA being capable of hybridizing with the mRNA coded by the DNA sequence represented by SEQ ID NO 1, any antisense mRNA as is described above, characterized in that it is coded by the nucleotide sequence complementary to that represented by SEQ ID NO 3, the said antisense mRNA being capable of hybridizing with the mRNA coded by the DNA sequence represented by SEQ ID NO 3.

The invention also relates to the recombinant polypeptides coded by the DNA sequences of the invention, the said recombinant polypeptides having an enzymatic activity equivalent to that of the CCRs in plants, and more particularly the recombinant CCRs coded by the sequences represented by SEQ ID NO 1 and SEQ ID NO 3, or by sequences derived from the latter according to the invention.

The invention more particularly relates to the recombinant polypeptides, and in particular the recombinant CCRs, such as are obtained by transformation of plant cells by integrating into their genome, in a stable manner, a recombinant nucleotide sequence as is defined below containing a DNA sequence according to the invention, in particular with the aid of a vector as is described below.

The expression "recombinant polypeptides" should be understood as meaning any molecule which has a polypeptide chain which is capable of being produced by genetic engineering, by the intermediary of a transcription phase of the DNA of the corresponding gene, leading to the obtaining of RNA which is subsequently transformed into mRNA (by suppression of introns), the latter being then translated by the ribosomes, in the form of proteins, the entire process being carried out under the control of suitable regulatory elements inside a host cell. The expression "recombinant polypeptides" used consequently does not exclude the possibility that the said polypeptides contain other groupings, such as glycosylated groupings.

The term "recombinant" of course indicates that the polypeptide has been produced by genetic engineering, since it results from expression, in a suitable cell host, of the corresponding nucleotide sequence which has been introduced beforehand into an expression vector used to transform the said cell host. However, this term "recombinant" does not exclude the possibility that the polypeptide is produced by a different process, for example by conventional chemical synthesis by the known methods used for synthesis of proteins, or proteolytic cleavage of molecules of larger size.

The invention more particularly relates to the CCR such as is present in lucerne cells and is represented by SEQ ID NO 2, or the CCR such as is present in maize cells and is represented by SEQ ID NO 4, the said CCRs being those obtained in an essentially pure form, by extraction and purification, from lucerne or maize, or any protein derived from the latter, in particular by addition and/or suppression and/or substitution of one or more amino acids, or any fragment resulting from the said CCRs or from their derived sequences, the said fragments and derived sequences being capable of having an enzymatic activity equivalent to that of the abovementioned CCRs.

The invention also relates to the nucleotide sequences which code for the CCR represented by SEQ ID NO 2 or SEQ ID NO 4, or any derived sequence or fragment of the latter, as are defined above, the said nucleotide sequences being characterized in that they correspond to all or part of the sequences represented by SEQ ID NO 1 or SEQ ID NO 3 respectively, or to any sequence derived from the latter by degeneration of the genetic code, and being nevertheless capable of coding for the CCRs or derived sequence or fragment of the latter, as are defined above.

The invention also relates to the complexes formed between the antisense mRNAs as are described above and the mRNAs according to the invention which are capable of coding for all or part of a CCR in plants.

The invention more particularly relates to the complex formed between the mRNA coded by the sequence SEQ ID NO 1 and the antisense mRNA coded by the sequence complementary to the sequence SEQ ID NO 1, and to the complex formed between the mRNA coded by the sequence SEQ ID NO 3 and the antisense mRNA coded by the sequence complementary to the sequence SEQ ID NO 3.

The invention more particularly relates to any recombinant nucleotide sequence (or recombinant DNA), characterized in that it contains at least one DNA sequence according to the invention chosen from those described above, the said DNA sequence being inserted into a heterologous sequence.

The invention more particularly relates to any recombinant nucleotide sequence as is described above containing, as the coding region, the nucleotide sequence represented by SEQ ID NO 1, or by SEQ ID NO 3, or any fragment or a nucleotide sequence derived from the latter, as are defined above, the said nucleotide sequences or the said fragment being inserted into a heterologous sequence, and being capable of coding for the CCR represented by SEQ ID NO 2, or by SEQ ID NO 4 respectively, or for a fragment of these CCRs, or for a protein derived from the latter, as are defined above.

The invention more particularly also relates to any recombinant nucleotide sequence containing, as the coding region, a nucleotide sequence complementary to that represented by SEQ ID NO 1, or by SEQ ID NO 3, or any fragment or any nucleotide sequence derived from this complementary sequence, as defined above, the said complementary sequences or the said fragment being inserted into a heterologous sequence and being capable of coding for an antisense mRNA which is capable of hybridizing with all or part of the mRNA which codes for a CCR in plants, and more particularly with all or part of the mRNA which codes for the CCR represented by SEQ ID NO 2, or by SEQ ID NO 4.

The recombinant DNAs according to the invention are further characterized in that they contain the elements necessary to regulate the expression of the nucleotide sequence which codes for a CCR, or of its complementary sequence which codes for an antisense mRNA according to the invention, in particular a promoter and a terminator of the transcription of these sequences.

Among the various promoters which can be used in the constructions of recombinant DNAs according to the invention there may be mentioned:
the endogenous promoter which controls the expression of the CCR in a plant, in particular the promoter situated upstream of the DNA sequence represented by SEQ ID NO 5 which codes, in eucalyptus, for the CCR represented by SEQ ID NO 6, or
promoters of a type which confers high expression, examples: $^{35}$S CAMV (described in Benfey et al. (1990), EMBO J., 9 (6), 1677–1684), EF1α (promoter of the gene of an elongation factor in protein synthesis, described by Curie et al. (1991), Nucl. Acids Res., 19, 1305–1310),
promoters of a type specific for particular expression in individual tissues, examples: promoter CAD (described by Feuillet C. (1993), Thesis of the University of Toulouse III), promoter GRP 1-8 (described by Keller and Baumgartner, (1991), Plant Cell., 3, 1051–1061) for expression in specific vascular tissues.

The invention also relates to any recombinant nucleotide sequence as is described above, also containing, as the coding region, at least one nucleotide sequence which codes for all or part of an mRNA which itself codes for an enzyme other than the CCR, which is found to be involved in a stage of the biosynthesis of lignins in plants, in particular the mRNA which codes for cinnamyl alcohol dehydrogenase (CAD), or also containing, as the coding region, at least one nucleotide sequence which codes for all or part of an antisense mRNA which is capable of hybridizing with the abovementioned mRNA, in particular with the mRNA which codes for CAD.

The abovementioned recombinant nucleotide sequences of the invention are advantageously obtained from vectors, into which are inserted the DNA sequences which code for an enzyme necessary for the biosynthesis of lignins in plants.

The abovementioned vectors are digested with the aid of suitable restriction enzymes in order to recover the said DNA sequences which are inserted there.

The latter are then inserted downstream of a suitable promoter, and upstream of a suitable terminator of expression, within the recombinant DNAs according to the invention.

The invention more particularly relates to the recombinant DNAs which contain the sequence represented by SEQ ID NO 1 or that represented by SEQ ID NO 3, such as are obtained by digestion of the abovementioned vectors, recovery of the DNA sequence of the invention and insertion of the latter in the sense 5'→3' within a heterologous DNA sequence containing a promoter and a terminator of the expression of the said sequence.

The invention also more particularly relates to the recombinant DNAs containing the sequence complementary to the sequence represented by SEQ ID NO 1 or that represented by SEQ ID NO 3, such as are obtained by digestion of the abovementioned vectors, recovery of the DNA sequence of the invention and insertion of the latter in the reverse sense, that is to say in the sense 3'→5', within a heterologous DNA sequence containing a promoter and a terminator of the expression of the complementary sequence.

By way of example of the terminator which can be used in such constructions there may be mentioned the 3' end of the gene of nopaline synthase of *Agrobacterium lumefaciens*.

Thus, generally, the recombinant nucleotide sequences according to the invention containing a DNA sequence which codes for a CCR (or a fragment of CCR or a derived protein), and/or other enzymes necessary for the biosynthesis of lignins, are obtained by recovery of the said DNA sequence from the abovementioned vectors and insertion of this sequence into the heterologous sequence, while the recombinant nucleotide sequences containing a DNA sequence which codes for an antisense mRNA according to the invention are obtained by recovery of the abovementioned DNA sequence and insertion of the latter in the reverse sense into the said heterologous sequence.

By way of illustration, all or part of the complementary DNA (cDNA) represented by SEQ ID NO 1 or SEQ ID NO 3 can be used for construction of the abovementioned recombinant DNAs, or also all or part of the genomic clone corresponding to a CCR (which corresponds to the abovementioned cDNAs+any introns). This genomic clone can be obtained using the cDNAs as probes to screen a genome bank, the latter itself being obtained by the method described by Sambrook, Fritsch and Maniatis, Molecular Cloning Laboratory Manual, Cold Spring Harbour Laboratory Press, 1989.

The invention also relates to any recombinant vector which can be used for the transformation of plants, characterized in that it contains a recombinant nucleotide sequence chosen from those described above, according to the invention, which is integrated into one of the sites of its genome which are not essential for its replication.

Among the abovementioned recombinant vectors which can be used for the transformation of plants, there may be mentioned: binary vectors derived from pBIN 19 (Bevan et al., (1984), Nucl. Acids Res., 12 (22), 8711–8721).

Examples of the construction of recombinant vectors according to the invention are described in the detailed description of the invention which follows.

The present invention also relates to a process for regulating the biosynthesis of lignins in plants, either by reducing or by increasing the amounts of lignins produced with respect to the normal amounts of lignins produced in these plants, the said process comprising a stage of transformation of cells of these plants with the aid of a vector containing:

the nucleotide sequence represented by SEQ ID NO 1 or by SEQ ID NO 3 or a fragment of the abovementioned nucleotide sequences, this fragment coding for an mRNA, this mRNA itself coding for a fragment of a CCR in plants, this CCR fragment having an enzymatic activity equivalent to that of the CCR represented by SEQ ID NO 2 or by SEQ ID NO 4, or of a nucleotide sequence derived from the abovementioned nucleotide sequences, or derived from the abovementioned fragment, in particular by mutation and/or addition and/or suppression and/or substitution of one or more nucleotides, this derived sequence coding for an mRNA, this mRNA itself coding for a derived protein having an enzymatic activity equivalent to that of at least one of the abovementioned CCRs, or a nucleotide sequence complementary to all or part of the nucleotide sequences represented by SEQ ID NO 1 or by SEQ ID NO 3 which code for an mRNA, or the fragment of these sequences, or the sequence derived from the latter, as are defined above, this complementary sequence coding for an antisense mRNA which is capable of hybridizing with one of the abovementioned mRNA, the said transformation being carried out in particular with the aid of a vector as is described above.

The invention more particularly relates to a process for reducing the amount of lignins produced by biosynthesis in plants, this process being carried out by transformation of the genome of these plants, incorporating:

at least one DNA sequence according to the invention as is described above which codes for an antisense mRNA which is capable of hybridizing with all or part of the mRNA which codes for the CCR represented by SEQ ID NO 2 or SEQ ID NO 4, or for a protein derived from the latter as is defined above, and, where appropriate, at least one DNA sequence which codes for an antisense mRNA which is capable of hybridizing with an mRNA which codes for an enzyme other than the CCR, which is found to be involved in a stage of the biosynthesis of lignins in plants, in particular the mRNa which codes for CAD, the said transformation being carried out:

either with the aid of a recombinant vector as is described above, containing a DNA sequence which codes for an antisense mRNA which is capable of hybridizing with the mRNA which codes for the CCR or for a derived protein, as is defined above, and, where appropriate, containing one or more DNA sequence(s) which code (s) for an antisense mRNA which is capable of hybridizing with an mRNA which codes for an enzyme other than the CCR as is defined above, or with the aid of several recombinant vectors, at least one of which contains a DNA sequence which codes for an antisense mRNA which is capable of hybridizing with the mRNA which codes for the CCR or for a derived proteins, as is defined above, while the other recombinant vector(s) contain(s) a DNA sequence which codes for an antisense mRNA which is capable of hybridizing with an mRNA which codes for an enzyme other than the CCR, as is defined above.

Another process for reducing the amount of lignins produced by biosynthesis in plants is that realized by transformation of the genome of these plants, incorporating:

at least one DNA sequence according to the invention represented by SEQ ID NO 1 or SEQ ID NO 3, or a fragment or a sequence derived from the latter, as are defined above, and, where appropriate, at least one DNA sequence which codes for all or part of an enzyme other than the CCR, which is found to be involved in a stage of the biosynthesis of lignins in plants, in particular a DNA sequence which codes for all or part of CAD, the said transformation being realized:

either with the aid of a recombinant vector as is described above containing the abovementioned DNA sequence according to the invention, or a fragment or a sequence derived from the latter, as are defined above, and, where appropriate, containing one or more DNA sequence(s) which code(s) for all or part of an enzyme other than the CCR, as is defined above, or with the aid of several recombinant vectors, at least one of which contains an abovementioned DNA sequence according to the invention, or a fragment or a sequence derived from the latter, as are defined above, while the other recombinant vector(s) contain(s) a DNA sequence which codes for all or part of an enzyme other than the CCR, as is defined above.

The latter method makes use of the co-suppression mechanism. Co-suppression has been observed when copies of the endogenous gene have been introduced into the genome. Although the mechanism of co-suppression is currently unknown, one of the most frequent hypotheses adopted is that negative regulation of the expression of the gene would come from production of a small proportion of antisense RNA derived from a transgene through reading of the "bad" strand of the transgene (Grierson et al., Trends Biotech., 9: 122–123).

The invention also relates to a process for reducing the amount of lignins produced by biosynthesis in plants, this process being carried out by transformation of the genome of these plants incorporating a DNA sequence as is described above according to the invention, which codes for an antisense sequence containing one (or more) catalytic domain(s) of a ribozyme bonded to one (or more) antisense mRNA(s), or fragment(s) of the antisense mRNA of the invention, the said transformation being carried out with the aid of a recombinant vector containing a recombinant nucleotide sequence according to the invention, itself containing the abovementioned DNA sequence.

It is important to note that the abovementioned methods allow transformed plants which have different levels of reduction of the CCR activity (depending on the level of insertion of the DNA sequence which codes for the antisense mRNA, the number of copies of this DNA sequence integrated into the genome . . . ), and therefore of lignin contents, to be arrived at.

The choice of transformants will therefore allow controlled modulation of the contents of lignins compatible with a normal development of the plant.

Generally, considering that the normal average content of lignins of a plant varies between about 15% and about 35% by weight of dry matter, the reduction in the content of lignins resulting from carrying out one of the abovementioned processes is advantageously such that the plants thus transformed have an average content of lignins which varies between about 10% and about 30%, or even between about 12% and about 32%.

By way of illustration, the content of lignins in a plant can be measured by a variant of the method of Johnson et al., (1961), T.A.P.P.I., 44, 793–798, which is described in detail in Alibert and Boudet (1979), Physiol., Veg., 17 (1), 67–74, the main stages of which are the following: after obtaining a powder of benzene alcohol containing lignins of plant material, the lignins are solubilized with acetyl bromide and analysed as a function of their absorption in ultraviolet light.

The invention more particularly relates to the use of the abovementioned processes for reducing the contents of lignins in plants to obtain genetically transformed fodder plants which have reduced lignin contents with respect to the normal contents of lignins in these plants, the digestibility of which is therefore found to be improved with respect to these same non-transformed plants.

Among the main fodder plants which can be transformed in the context of the present invention there may be mentioned: lucerne, fescue, maize for silaging etc . . . .

The invention also relates to the use of the abovementioned processes for reducing the contents of lignins in plants to obtain genetically transformed plants, and more particularly trees, having reduced lignin contents with respect to the normal contents of lignins in these plants, these plants or trees being particularly advantageous for use in the context of the production of paper pulp.

A third potential field of application of the abovementioned processes for negative regulation of the expression of the gene of the CCR relates to stimulation of the growth of the transformed plants. Various arguments (Sauter and Kende, 1992, Plant and Cell Physiology, 33 (8):1089) emphasize that early and rapid lignification is a restraint on cell enlargement and thus on the growth of plants. The use of the abovementioned processes is thus capable of allowing better growth and therefore better yields for the plants with reduced lignification transformed in this way.

The invention also relates to a process for increasing the amount of lignins produced by biosynthesis in plants, this process being carried out by transformation of the genome of these plants, incorporating:

at least one DNA sequence according to the invention represented by SEQ ID NO 1 or SEQ ID NO 3, or a fragment or a sequence derived from the latter, as are defined above, and, where appropriate, at least one DNA sequence which codes for all or part of an enzyme other than the CCR, which is found to be involved in a stage of the biosynthesis of lignins in plants, in particular a DNA sequence which codes for all or part of CAD, the said transformation being carried out:

either with the aid of a recombinant vector as is described above containing the abovementioned DNA sequence according to the invention, or a fragment or a sequence derived from the latter, as are defined above, and, where appropriate, containing one or more DNA sequence(s) which code(s) for all or part of an enzyme other than the CCR, as is defined above, or with the aid of several recombinant vectors, at least one of which contains an abovementioned DNA sequence according to the invention, or a fragment or a sequence derived from the latter, as are defined above, while the other recombinant vector(s) contain(s) a DNA sequence which codes for all or part of an enzyme other than the CCR, as is defined above.

Generally, always considering that the normal average content of lignins in a plant varies between about 15% and about 35% by weight of dry matter, the increase in the content of lignins resulting from carrying out the abovementioned process is advantageously such that the plants thus transformed have an average content of lignins which varies between about 20% and about 40%, or even between about 18% and about 38%.

The invention more particularly relates to the use of the abovementioned process for increasing the content of lignins in plants (also called a process for over-expression of the gene of the CCR) to obtain genetically transformed plants having increased lignin contents with respect to the normal contents of lignins in these plants, of which the resistance properties to environmental attacks, in particular to parasitic attacks, are thus found to be improved with respect to these same non-transformed plants. In the latter case, it is particularly advantageous to use, in combination with the CCR gene, or a derived sequence, in the abovementioned vectors, specific promoters which are expressed particularly in the tissues of the surface and/or in response to wounding.

Furthermore, the invention also relates to the use of the abovementioned process of over-expression of the gene of the CCR for improving the growth of the plants genetically transformed in this way, in particular in certain sectors, such as horticulture or arboriculture, where it is desirable to obtain plants of reduced size.

Finally, the benzene rings of lignin have a higher intrinsic energy than the aliphatic chains of the glucose residues of cellulose. The increase by the abovementioned process of the invention in the proportion of lignin in plants used as fuels thus allows an improvement in the energy potential of these combustible plants.

In the two cases of negative regulation or of over-expression of the CCR, it is entirely foreseeable that the modulation of this activity has repercussions on the content of lignins in the transformed plants. In fact, the CCR, of which the level of activity is very low in the plant, seems to be the regulatory enzyme of lignin synthesis.

Regarding the transformation techniques used to carry out one of the processes of the invention which are described above, the following techniques will advantageously be used:

A) The technology of transformation by the intermediary of the plasmid Ti of *Agrobacterium tumefaciens* described by Bevan (1984) Nucleic Acid Research, 12, 8711–8721. This essentially makes use of the method of co-culture, and involves a co-transformation with a selection gene to be able to identify the transformants.

It is particularly applicable to dicotyledons, e.g.: tobacco, lucerne, rape.

B) The technique of direct transfer of genes by biolistics described in detail by (Zumbrum et al., 1989, Technique 1, 204–216; Sanford et al., 1991, Technique 3, 3–16).

This technique involves combination of the recombinant DNA according to the invention with microparticles of gold or tungsten, which are propelled with the aid of a particle gun onto the tissue to be transformed. It will be applied in particular to the transformation of species which are unaffected by Agrobacteria.

In the two abovementioned cases, verification of the presence of the recombinant DNA according to the invention will be carried out by hybridization experiments of the Southern type and gene amplification (polymerase chain reaction) with the aid of probes and oligonucleotide primers resulting from, in particular, the sequence SEQ ID NO 1 or SEQ ID NO 3.

The invention also relates to the cells of plants transformed by a vector according to the invention, in particular by the techniques described above, and containing a DNA sequence according to the invention integrated in their genome in a stable manner.

The invention also relates to the transformed plants such as are obtained by culture of the abovementioned transformed cells.

The transformed plants can then be propagated sexually or vegetatively in vitro or in natura.

The invention also relates to the fragments of plants, in particular fruits, seeds or pollen, transformed by incorporation into their genome of a DNA sequence according to the invention with the aid of the abovementioned recombinant vectors.

The invention also relates to antibodies directed against the recombinant polypeptides of the invention, and more particularly those directed against the abovementioned recombinant CCRs.

Such antibodies can be obtained by immunization of an animal with these polypeptides, followed by recovery of the antibodies formed.

It goes without saying that this production is not limited to polyclonal antibodies.

It is also applied to any monoclonal antibody produced by any hybridoma which is capable of being formed by conventional methods from the splenic cells of an animal, in particular the mouse or rat, immunized against one of the purified polypeptides of the invention on the one hand and cells of a suitable myeloma on the other hand, and of being selected by its capacity to produce monoclonal antibodies which recognize the abovementioned polypeptide initially used for immunization of the animals.

The invention also relates to the use of the abovementioned antibodies directed against the recombinant polypeptides of the invention for carrying out a method for detection or analysis of the CCRs in plants from samples taken from the latter.

It is appropriate to state that the nucleotide sequences represented by SEQ ID NO 5, SEQ ID NO 7, SEQ ID NO 9 and SEQ ID NO 11 which code, respectively, for the CCR of eucalyptus represented by SEQ ID NO 6, the CCR of poplar represented by SEQ ID NO 8, the CCR of fescue represented by SEQ ID NO 10 and the CCR of tobacco represented by SEQ ID NO 12, as well as the sequence represented by SEQ ID NO 13 which codes for the protein represented by SEQ ID NO 14 derived from the abovementioned CCR of eucalyptus, are excluded from the nucleotide sequences of the invention and their abovementioned use.

Furthermore, the sequences complementary to the nucleotide sequences SEQ ID NO 5, SEQ ID NO 7, SEQ ID NO 9, SEQ ID NO 11 and SEQ ID NO 13, and also the fragments or sequences derived from these nucleotide sequences or from their complementary sequences, inasmuch as these fragments and derived sequences are identical to fragments and derived sequences as are defined above, nucleotide sequences represented by SEQ ID NO 1 and SEQ ID NO 3 or their complementary sequences, are excluded from the nucleotide sequences of the invention and their abovementioned use.

The following are also excluded from the context of the present invention:

the mRNAs coded by the DNA sequences represented by SEQ ID NO 5, SEQ ID NO 7, SEQ ID NO 9, SEQ ID NO 11 and SEQ ID NO 13, or coded by a fragment or a sequence derived from these DNA sequences, inasmuch as this fragment or derived sequence are identical to fragments and derived sequences, as are defined above, of the sequences represented by SEQ ID NO 1 and SEQ ID NO 3, the antisense mRNAs made up of nucleotides complementary to the abovementioned mRNAs, the polypeptides represented by SEQ ID NO 6, SEQ ID NO 8, SEQ ID NO 10, SEQ ID NO 12 and SEQ ID NO 14, and also any fragment or sequence derived from the abovementioned polypeptides, inasmuch as this fragment or derived sequence are identical to the fragments and derived sequences, as are defined above, of the polypeptide sequences represented by SEQ ID NO 2 and SEQ ID NO 4.

The invention will be detailed further in the description which follows for the preparation of the CCR in purified form in eucalyptus, and of the cDNA which codes for the CCR of eucalyptus, lucerne and maize.

A) Preparation of the Purified CCR of Eucalyptus and of the cDNA Which Codes for a CCR of Eucalyptus 1. Purification of the CCR of Eucalyptus The CCR has been the subject of a very limited number of studies. Among the few publications relating to it, there may be mentioned:

Wengenmayer H., Ebel J., Grisebach H., 1976—Enzymatic synthesis of lignin precursors, purification and properties of a cinnamoyl-CoA: NADPH reductase from cell suspension cultures from soybean (*Glycine max*), Eur. J. Biochem., 65, 529–536.

Luderitz T., Grisebach H., 1981—Enzymatic synthesis of lignin precursors, comparison of cinnamoyl: CoA reductase and cinnamyl alcohol dehydrogenase: NADP dehydrogenase from spruce (*Picea abies L.*) and soybean (*Glycine max L.*), Eur. J. Biochem., 119: 115–127.

Sarni F., Grand C., Boudet A. M., 1984—Purification and properties of cinnamoyl-CoA reductase and cinnamyl alcohol dehydrogenase from poplar stems (*Populus x euramericana*). Eur. J. Biochem., 139: 259–265.

The work described below has contributed to the definition of an original, simple and rapid protocol for the purification of the CCR of eucalyptus. This protocol is also more effective than those described previously in the literature. In fact, it has allowed, for the first time, the preparation of enzyme purified to homogeneity in amounts sufficient to obtain internal peptide sequences and to lead in time to cloning of the corresponding cDNA.

All the stages of purification of the CCR were carried out at 4° C.

1. Preparation of a Crude Extract of the Xylem of Eucalyptus.

The plant material was obtained by "scraping" a xylem-enriched tissue fraction from branches of *Eucalyptus gunnii* aged 5 years.

300 g xylem, frozen beforehand in liquid nitrogen, were reduced to a powder with the aid of a coffee grinder. The ground material thus obtained was homogenized in one litre of extraction buffer (100 mM Tris-HCl pH 7.6, 2% PEG 6000, 5 mM DTT, 2% PVPP), filtered over two layers of Miracloth, and brought to 30% saturation in ammonium sulphate. After centrifugation at 15,000×g for 30 minutes, the sediment obtained is resuspended in 60 ml of buffer 1 [20 mM Tris-HCl p7.5, 5 mM DTT (dithiothreitol), 5% ethylene glycol]. The extract thus obtained is "clarified" by a centrifugation at 10,000×g for 15 min, and then desalinated by passage over Sephadex G25 equilibrated in buffer 1.

2. Affinity Chromatography on Red Sepharose.

The crude desalinated extract is deposited on a "Red Sepharose" affinity column (1.5×19 cm, Pharmacia), equilibrated in buffer 1. After a first rinsing of the column with 50 ml buffer 1, the proteins are eluted by a linear gradient of Tris from 20 mM to 1.5 M Tris-HCl pH 7.5, containing 5 mM DDT and 5% ethylene glycol. The total volume of the gradient is 200 ml and the flow rate is 36 ml/h. The fractions having a CCR activity are combined and desalinated by passage over a Sephadex G25 column equilibrated in buffer 1.

3. Anion Exchange Chromatography on MonoQ.

The fractions thus combined and desalinated are chromatographed over a MonoQ anion exchange column (HR 5/5, Pharmacia). Elution of the proteins is carried out by application of a linear gradient from 20 to 300 mM of Tris-HCl pH 7.5 containing 5% ethylene glycol and 5 mM DTT. The total volume of the gradient is 50 ml and the flow rate is 1 ml/min. As in the preceding stage, the fractions containing the active CCR enzyme are combined and desalinated, but in this case the equilibration buffer of the Sephadex G25 columns is a 20 mM phosphate buffer pH 7.6 containing 5 mM DTT (buffer 2).

4. Affinity Chromatography on "Mimetic Red"

The group of CCR fractions thus obtained is deposited on a Mimetic Red 2 A6XL column (ACL, Cambridge). The column is washed beforehand with 30 ml buffer 2 containing 8 mM NAD. The aim of this washing is to eliminate enzymes which function specifically with NAD as a cofactor, such as malate dehydrogenase, which is copurified with the CCR in the preceding stages. Specific elution of the CCR is obtained by application of an NADP gradient (15 ml) of 0–8 mM in buffer 2. The fractions containing the pure and active CCR are stored at −80° C., after addition of a stabilizer (ethylene glycol to a final concentration of 5%).

The purified enzyme thus obtained has a specific activity of 451 nKat/mg protein, using feruloyl-CoA as the substrate. The yield obtained (36 µg pure protein per 300 g plant starting material) does not reflect the proportion of CCR in planta, and in fact in a major effort to eliminate the maximum contamination at each purification stage, only the fractions having a very high CCR activity are treated in the following stage. The purification factor obtained by this protocol is 282.

II Characterization of the CCR

The CCR of eucalyptus is a monomer of 38 kD, as demonstrated by convergent results obtained for the size of the native enzyme by exclusion chromatography over Superose 6 (Pharmacia) and for the size of the monomer sub-unit on denaturing electrophoresis gel. The isoelectric point, estimated by chromatography over MonoP (Pharmacia) is close to 7.

Investigation of the optimum pH and buffer shows that measurement of the CCR activity as was initially described (Luderitz and Grisebach, 1981) is excellently suitable for measurement of the CCR activity of eucalyptus (100 mM phosphate buffer, pH 6.25).

The purity of the CCR present in the state of a single band on monodimensional electrophoresis gel (SDS PAGE) was confirmed by a single spot being obtained after bidimensional electrophoresis and staining with silver.

III Preparation of the cDNA Which Codes for the CCR of Eucalyptus

In order to avoid any problem of undetectable residual contamination, the pure enzyme was subjected to preparative electrophoresis under semi-denaturing conditions and digested in situ in the gel. The digestion was carried out with the aid of endolysine C, which cuts proteins specifically after lysine residues, allowing the preparation of relatively long peptides. The peptides resulting from the digestion were separated by reverse phase HPLC, and some of them were sequenced with the aid of a protein microsequencer (Applied Biosystems 470). The sequences of these internal peptides are shown below:

peptide 8 (a) (SEQ ID NO: 15) Asn-Trp-Tyr-Cys-Tyr-Gly-Lys (b) (SEQ ID NO: 16) His-Leu-Pro-Val-Pro-X-Pro-Pro-Glu-Asp-Ser-Val-Arg X representing any amino acid peptide 10 (SEQ ID NO: 17) Thr-Tyr-Ala-Asn-Ser-Val-Gln-Ala-Tyr-Val-His-Val-Lys peptide 13 (SEQ ID NO: 18) Gly-Cys-Asp-Gly-Val-Val-His-Thr-Ala-Ser-Pro-Val-Thr-Asp-Asp peptide 17 (SEQ ID NO: 19) Leu-Arg-Asp-Leu-Gly-Leu-Glu-Phe-Thr-Pro-Val-Lys peptide 18 (SEQ ID NO: 20) Gly-Asp-Leu-Met-Asp-Tyr-Gly-Ser-Leu-Glu-Glu-Ala-Ile-Lys The cDNA which codes for the CCR was obtained by screening, with the aid of oligonucleotides of a cDNA bank constructed in the phage λ ZAPII (commercially available vector, Stratagène) from messengers extracted from the xylem of *Eucalyptus gunnii*. 600,000 phages were screened with the aid of a group of degenerated oligonucleotides marked at the 3' end with $^{32}$phosphorus with the aid of a terminal transferase. The oligonucleotide sequences used for the screening were determined from the abovementioned internal peptide sequences. Since these peptides were generated by cutting with endolysine C, a lysine was added in the first position to allow production of oligonucleotides of less degeneration. In fact, this amino acid can be coded only by two codons, forms part of the amino acids of which the code is degenerated less, and consequently is entirely suitable for preparation of oligonucleotides from peptide sequences.

The oligonucleotide sequences used for screening the cDNA bank of eucalyptus which are derived from the amino acids underlined (I=inosine) are indicated below:

peptide 8 (a) (SEQ ID NO: 21) Lys-Asn-Trp-Tyr-Cys-Tyr-Gly-Lys poligonucleotide 8 (SEQ ID NO: 22) AA(A/G)AA(C/T)TGGTA(C/T)TG(C/T)TA(T/C)GGIAA peptide 13 (SEQ ID NO: 23) Lys-Gly-Cys-Asp-Gly-Val-Val-His-Thr-Ala-Ser-Pro-Val-Thr-Asp-Asp oligonucleotide 13 (SEQ ID NO: 24) AA(G/A)GGITG(C/T)GA(C/T)GGIGTIGTICA peptide 17 (SEQ ID NO: 25) Lys-Leu-Arg-Asp-Leu-Gly-Leu-Glu-Phe-Thr-Pro-Val-Lys oligonucleotide 17 (SEQ ID NO: 26) GA/(G/A)TT(C/T)ACICCIGTIAA peptide 18 (SEQ ID NO: 27) Lys-Gly-Asp-Leu-Met-Asp-Tyr-Gly-Ser-Leu-Glu-Glu-Ala-Ile-Lys oligonucleotide 8 (SEQ ID NO: 28) AA(G/A)GGIGA(C/T)(C/T)TIATGGA(C/T)TA(C/T)GG The hybridization conditions used for the screening are as follows: the prehybridization is carried out for 6 to 7 hours in 5×SSPE, 0.25% skimmed milk powder and 0.05% SDS (sodium dodecyl sulphate) at 42° C. The hybridization is carried out in this same solution in the presence of 4 oligonucleotides marked at 3' by ddATPα$^{32}$P, for 24 hours at 42° C. At the end of these 24 hours of hybridization, the filters are washed three times for 15 minutes in 2×SSC and 0.1% SDS and then brought into contact with an autoradiography film for 24 hours at −80° C. The phages which hybridize with the group of oligonucleotides were purified by 2 supplementary screening cycles ("plate purification"). Once purified, the six positive clones were tested with each of the oligonucleotides taken independently. One phage reacted positively with the 4 oligonucleotides, and was treated in order to "excise" the recombinant Bluescript plasmid following the manufacturer's instructions (Stratagène). The restriction map of the insert (coding for the CCR) contained in this plasmid is shown in diagram form on FIG. 1.

IV Characterization and Identification of the cDNA of the CCR

The amino acid sequences (represented by SEQ ID NO 6) deduced from the nucleotide sequence (represented by SEQ ID NO 5) codes for a protein of 335 amino acids, the molecular weight of which is 36.5 kD and the isoelectric point of which is about 5.8. It is important to emphasize that all the peptide sequences obtained from the purified CCR are found in the peptide sequence deduced from the nucleotide sequence of the cDNA.

Investigations of homologies with already-existing clones were carried out using the BLAST and FASTA programs in all the available protein and nucleic banks. A significant homology was found with another reductase of the metabolism of phenolic compounds, dihydroflavonol reductase (DFR). The identity is about 40% and the similarity approaches 20% between the peptide sequence deduced from the cDNA of the CCR and the sequences of the various dihydroflavonol reductases catalogued in the banks, which confirms that the clone identified differs from a clone which codes for a DFR.

V Production of Active Recombinant CCR in E. coli

For all further work in the identification of the cDNA of the CCR, the recombinant protein was produced in E. coli and its enzymatic activity was investigated. The experimental details of this approach are described below.

1—Introduction of the cDNA into the Expression Vector pT7-7.

In order to be able to clone the cDNA in the expression vector pr7-7 (commercially available) under the control of the promoter of T7 polymerase, we had to introduce an NdeI site at the ATG of the cDNA. This was carried out with the aid of a Taq polymerase during a reaction for gene amplification by PCR (polymerase chain reaction) between a muted oligonucleotide and a commercial primer, T7, situated on the Bluescript downstream of the 3' end of the cDNA. The amplification product obtained is digested by KpnI, this site is then repaired with the aid of the Klenow fragment of DNA polymerase I before the fragment is subjected to digestion by NdeI, and the fragment obtained, containing an NdeI site at 5' and a free end at 3', is then inserted with the aid of a T4 DNA ligase into the vector PT7-7, which has been opened beforehand by NdeI and SmaI.

The sequence of the abovementioned muted oligonucleotide is indicated below.

The bases underlined and in italics were modified with respect to the initial sequence, allowing the creation of an NdeI site (CATATG):

5'GGCAATCCC*CAT*ATGCCCGTCGACGC3 (SEQ ID NO: 29)

2. Over-expression of the CCR in E. coli BL21

The construction thus obtained is introduced into the strain E. coli BL21 (commercially available), which carries on its chromosome the gene of T7 polymerase under control of the promoter lac UV5, a promoter which can be induced by IPTG. The recombinant culture is cultured at 37° C. until the OD measured is 1 at 600 nm, and the production of the CCR is then induced by addition of IPTG (0.25% finally) to the culture medium. Samples are taken at various times after the induction, and the cells are lysed by the protocol described by Grima-Pettenati et al. (1993). After centrifugation, the supernatant containing the soluble proteins is used to measure the CCR activity and to visualize the production of CCR, after electrophoresis under denaturing conditions. The appearance of a polypeptide of about 38 kD, the intensity of which increases with the post-induction time and which does not exist in negative controls (strain BL21 containing only the vector pT7-7 without the insert), is found. Furthermore, the final proof of the identity of the CCR clone is provided by measurement of a CCR activity (about 7 nKat/ml culture after induction for 3 h at 37° C.) in the protein extracts originating from strains of BL21 containing only pT7-7+cDNA CCR.

The vector called pEUCCR (shown on FIG. 2), containing the sequence represented by SEQ ID NO 5 cloned in the Bluescript vector, has been deposited in culture in cells of E. coli DH5α at the Collection Nationale de Culture de Micro-organismes [National Culture Collection of Microorganisms] (CNCM) of the Institut Pasteur in Paris (France) on March 17th, 1994 under no. I-1405.

LEGEND TO THE FIGURES

FIG. 1: Restriction map of the cDNA which codes for the CCR of eucalyptus.

Figure 2:
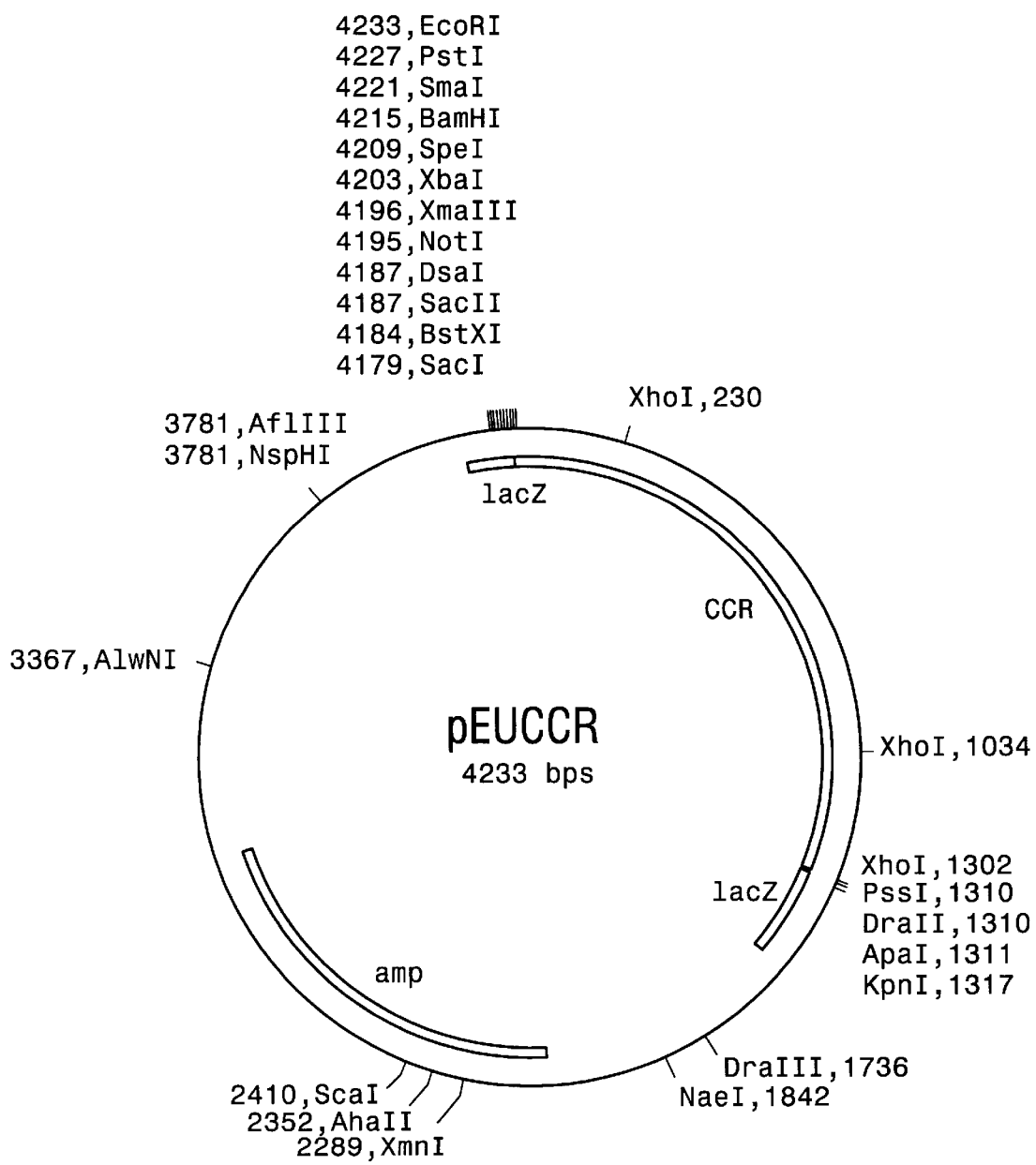

FIG. 2: Schematic representation of the plasmid pEUCCR containing the sequence represented by SEQ ID NO 5 (and identified by CCR in the plasmid pEUCCR).

Figure 3:
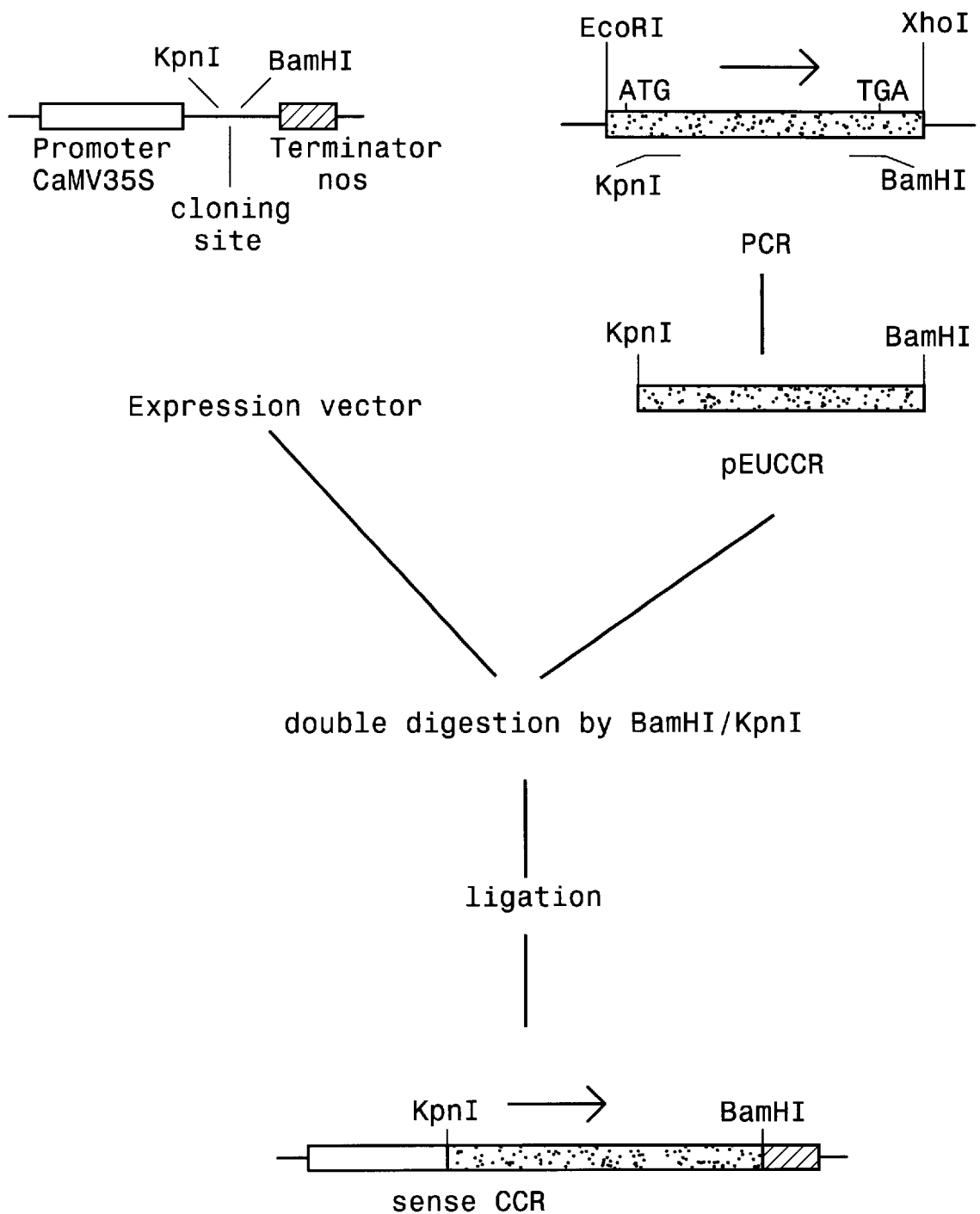

FIG. 3: Schematic representation of the construction of a vector containing a DNA sequence which codes for the CCR of eucalyptus according to the invention (or sense CCR vector).

Figure 4:
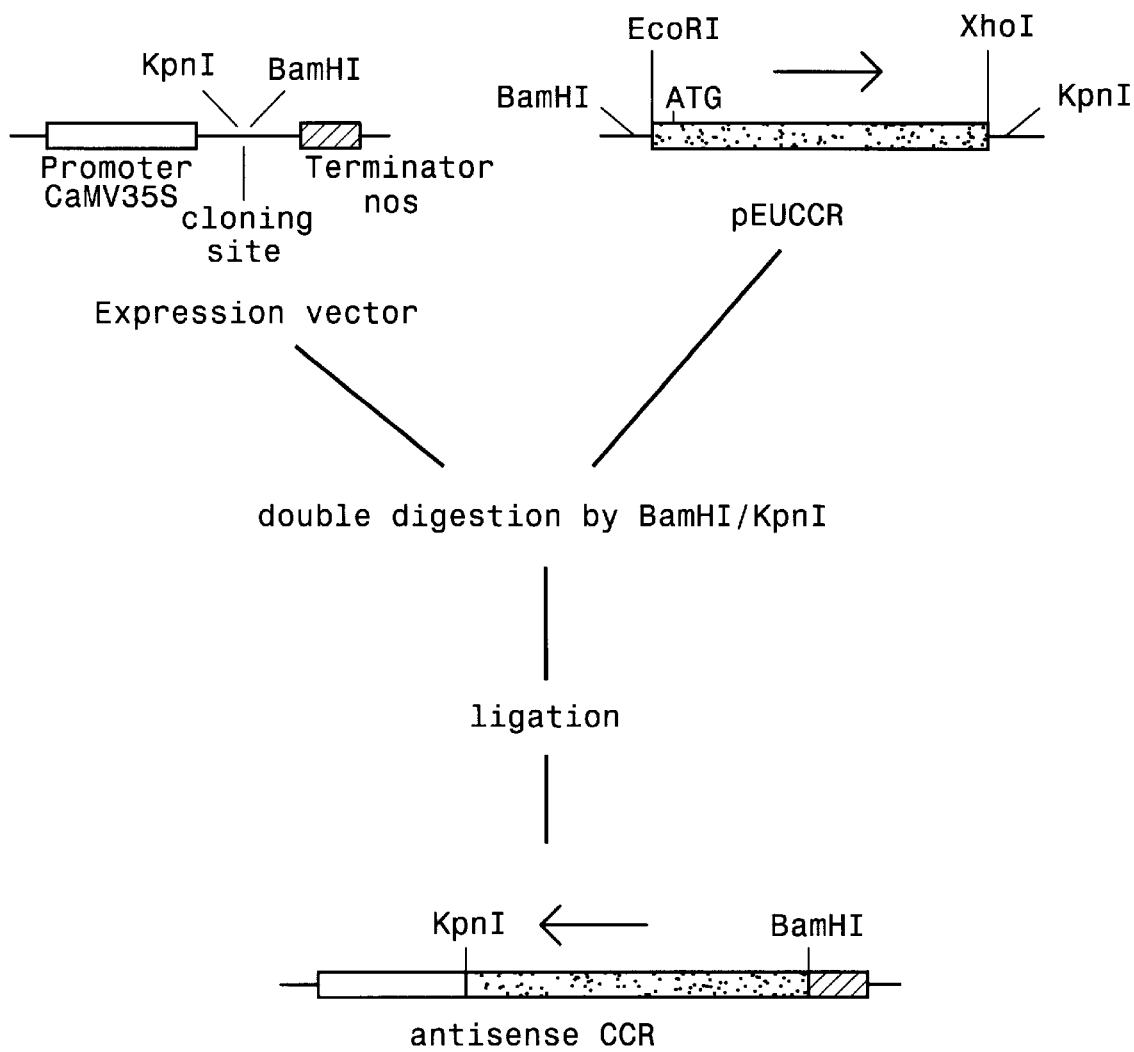

FIG. 4: Schematic representation of the construction of a vector containing a DNA sequence which codes for an antisense RNA which is capable of hybridizing with the mRNA which codes for the CCR of eucalyptus according to the invention (or antisense CCR vector).

REGARDING THE DNA SOURCE SERVING FOR THE CONSTRUCTION OF AN ANTISENSE (or sense) VECTOR The antisense RNA is preferentially derived from the sequence contained in the clone pEUCCR. This sequence can be obtained in various ways:

1) by cutting the DNA (cDNA) sequence of the CCR contained in pEUCCR with suitable restriction enzymes,
2) by performing a gene amplification (PCR) with the aid of defined oligonucleotides such that the desired DNA fragment is synthesized.

The DNA fragment thus obtained is cloned in an expression vector of plants downstream of a promoter and upstream of a terminator. The cloning is carried out such that the DNA fragment is inserted in reverse orientation with respect to the promoter. In this new vector, the strand which was initially the matrix strand becomes the coding strand and vice versa.

The new vector codes for an RNA, the sequence of which is complementary to the messenger RNA sequence deduced from the sequence contained in pEUCCR.

The 2 RNAs are thus complementary by their sequence and also by their orientation (5'–3').

As the source of DNA for transcription of the antisense RNA, it is appropriate to use a cDNA clone such as that contained in pEUCCR.

Example of Antisense Cloning (cf. FIG. 4)

The cDNA of the CCR is obtained by a double digestion (BamHI and KpnI) from the vector pEUCCR. The DNA fragment thus liberated is separated physically from the cloning vector by an agarose gel electrophoresis (Bluescript).

The part of the gel containing this DNA fragment is cut out and treated to obtain the purified DNA (several methods can be used, including "low-melting agarose" described in Sambrook et al. loc. cit., and Gene Clean, the kit of which is commercially available).

The fragment which carries the BamHI and KpnI ends is "ligated" with an expression vector of plants which has been digested beforehand by these same enzymes, chosen such that the cDNA is inserted in reverse orientation with respect to the promoter $^{35}$S. The strand which will be transcribed in the plants will in this case be the non-coding strand.

Example of Sense Cloning (cf. FIG. 3)

In this case, there are no "practical" restriction sites for realizing translational fusion with the promoter $^{35}$S of the expression vector. More convenient new sites were inserted with the aid of the gene amplification technique (PCR). Two oligonucleotides have been defined at 5' and 3' of the cDNA, to which have been added the sequences of sites recognized by KpnI and BamHI (NB: these are the same sites as have been used for the abovementioned antisense cloning, but are positioned differently with respect to the 5'–3' orientation).

Gene amplification leads to a fragment containing all the coding sequence of the cDNA flanked by 2 restriction sites being obtained. The subsequent procedure is identical to that described for the antisense construction.

In this case, however, a fusion of the promoter in phase with the ATG of the CCR has been realized, which must lead to an over-expression of the messenger RNA and therefore of the protein CCR.

The examples of cloning of sense and antisense sequences described above in the case of the CCR of eucalyptus can also be applied in the case of the CCR of lucerne and that of maize.

B) Preparation of the cDNA Which Codes for the CCR of Lucerne (*Medicago truncatula*)

Characteristics of the cDNA Bank:

The bank used was constructed from total RNA extracts of roots of *Medicago truncatula* in the vector λZAPII ("ZAP-cDNA synthesis" kit from Stratagène).

Screening of the cDNA Bank:

Probe:

Screening of the lucerne bank was carried out with the aid of the cDNA which codes for the CCR of eucalyptus. A fragment of 800 bp (Xho-Xho) of pEUCCR marked by the technique of random priming was used as the probe.

Display of the Bank and Imprints on Nitrocellulose Filter:

300,000 clones were displayed and then transferred to the nitrocellulose filter (Schleicher & Schuell). For this, the filters were placed on the culture boxes for 5 min and then immersed successively in the following solutions:

| 1.5M NaCl/0.5M NaOH | 5 min |
| 1.5M NaCl/0.5M Tris pH 8 | 5 min |
| 3 × SSC | 2 min | heating for 2 hours at 80° C.

Prehybridization-hybridization:

The filters were prehybridized for 12 hours and then hybridized for 24 hours at 37° C. in the following medium:

Prehybridization and hybridization medium:

formamide 20% dextran 10%

NaCl 1 M

DNA of salmon sperm (1 mg/ml)

0.2% polyvinylpyrrolidone 0.2% BSA 0.2% ficoll 0.05 M Tris-HCl pH 7.5

0.1% sodium pyrophosphate

1% SDS.

After hybridization, the filters were washed 2× for 10 min at ambient temperature in 2×SSC-1% SDS, and then 2× for 30 min at 55° C. in the same solution.

After autoradiographic exposure of the filters, 15 positive lysis areas were identified. These lysis areas were purified by two additional screening cycles under the hybridization conditions described above.

Excision in vivo:

From the positive clones, the Bluescript plasmid of the λ phage was excised by the in vivo excision protocol of the "ZAP-cDNA synthesis kit".

The CCR cDNA of lucerne:

The cDNA which codes for the CCR of lucerne, 1,404 bp in size, is inserted into the EcoRI (5' side) and Xho (3' side) sites of the Bluescript vector. It is made up of the following parts:

a non-translated transcribed 5' part of 167 bp, a region of 1,028 bp which codes for a protein of 342 amino acids, a non-translated transcribed 3' part of 209 bp.

The cDNA obtained is represented by SEQ ID NO 1, and the sequence of amino acids deduced from this cDNA is represented by SEQ ID NO 2.

C) Preparation of the cDNA Which Codes for the CCR of Maize

Characteristics of the cDNA Bank:

The bank used was constructed from total RNA extracts from the roots of maize (variety AMO 406) deprived of iron, in the vector λZAP ("ZAP-cDNA synthesis" kit from Stratagène).

Screening of the cDNA Bank:

Probe:

Screening of the maize bank was carried out with the aid of the CCR cDNA of eucalyptus. A fragment of 800 bp (Xho-Xho) of pEUCCR marked by the technique of random priming was used as the probe.

Display of the Bank and Imprints on Nitrocellulose Filter:

500,000 clones were displayed and then transferred to the nitrocellulose filter (Schleicher & Schuell). For this, the filters were placed on the culture boxes for 5 min and then immersed successively in the following solutions:

| | |
|---|---|
| 1.5M NaCl/0.5M NaOH | 5 min |
| 1.5M NaCl/0.5M Tris pH 8 | 5 min |
| 3 × SSC | 2 min | heating at 80° C. for 2 hours.
Prehybridization-hybridization:
The filters were prehybridized for 12 hours and then hybridized for 24 hours at 55° C. in the following medium:
Prehybridization and hybridization medium:
3×SSC
0.5% SDS
0.1% powdered milk DNA of salmon sperm (1 mg/ml).

After hybridization, the filters were washed 2× for 10 min at ambient temperature in 3× SSC-0.5% SDS, and then 2× for 45 min at 60° C. in the same solution.

After autoradiographic exposure of the filters, 20 positive lysis areas were identified. These lysis areas were purified by 3 additional screening cycles under the hybridization conditions described above.

Excision in vivo:

From the positive clones, the Bluescript plasmid of the λ phage was excised by the in vivo excision protocol of the "ZAP-cDNA synthesis kit".

The cDNA obtained is represented by SEQ ID NO 3, and the sequence of amino acids deduced from this cDNA is represented by SEQ ID NO 4.

What is claimed is:

1. A method of producing transgenic plants within which the biosynthesis of lignins is regulated either in the sense of an increase, or in the sense of a reduction of the lignin levels produced, relative to the normal lignin levels produced in plants comprising:

transforming plant cells with a recombinant nucleotide sequence comprising one or more coding regions, wherein said coding regions are selected from the group consisting of:

the nuclcotide sequence represented by SEQ ID NO: 1, coding for a mRNA, said mRNA coding for the Cinnamoyl CoA Reductase (CCR) of lucerne represented by SEQ ID NO: 2; and the nucleotide sequence represented by SEQ ID NO: 3, coding for a mRNA, said mRNA coding for the CCR of maize represented by SEQ ID NO: 4, and the nucleotide sequence fully complementary to that represented by SEQ ID NO: 1, or SEQ ID NO: 3.

2. An isolated DNA sequence comprising:
   the nuclcotide sequence represented by SEQ ID NO: 1, coding for a mRNA, said mRNA coding for the Cinnamoyl CoA Reductase (CCR) represented by SEQ ID NO: 2, or the nucleotide sequence represented by SEQ ID NO: 3, coding for a mRNA, said mRNA coding for a protein represented by SEQ ID NO: 4.

3. An isolated DNA sequence comprising:
   the nucleotide sequence fully complementary to that represented by SEQ ID NO: 1 or the nucleotide sequence fully complementary to that represented by SEQ ID NO: 3.

4. An isolated mRNA selected from
   the mRNA coded by the DNA sequence represented by SEQ ID NO: 1 and the mRNA coded by the DNA sequence represented by SEQ ID NO: 3.

5. An anti sense mRNA comprising nucleotides fully complementary to a mRNA according to claim 4.

6. An isolated nucleotide sequence coding for the CCRs represented by SEQ ID NO: 2 or SEQ ID NO: 4.

7. An isolated complex formed between an anti sense mRNA according to claim 5, and a CCR mRNA.

8. An isolated recombinant nucleotide sequence comprising at least one DNA sequence according to claim 2, said sequence being inserted in a heterologous sequence.

9. An isolated recombinant nucleotide sequence, comprising at least one fully complementary DNA sequence according to claim 3, inserted in a heterologous sequence.

10. A process for the regulation of the biosynthesis of lignins in a plant, either by reducing, or by increasing the levels of lignin produced, relative to the normal levels of lignins produced in said plant, said process comprising the step of transforming cells of said plant using a vector containing a nucleotide sequence according to claim 2.

11. A plant, plant fragment, cell, fruit, seed, or pollen, transformed by incorporation of at least one nucleotide sequence selected from the group consisting of:

the nucleotide sequence represented by SEQ ID NO: 1, coding for a mRNA, said mRNA coding for the Cinnamoyl CoA Reductase (CCR) of lucerne represented by SEQ ID NO: 2, the nucleotide sequence represented by SEQ ID NO: 3, coding for a mRNA, said mRNA coding for the CCR of maize represented by SEQ ID NO: 4, and the nucleotide sequence fully complementary to that represented by SEQ ID NO: 1 and SEQ ID NO: 3.

12. An isolated recombinant nucleotide sequence according to claim 9 wherein said at least one fully complementary DNA sequence is operatively linked to at least one of a promoter or a terminator.

13. An isolated recombinant vector comprising a recombinant nucleotide sequence according to claim 12.

14. A process for reducing the biosynthesis of lignins in plants, relative to the normal levels of lignins produced in these plants, said process comprising transforming cells of said plants with a vector containing a nucleotide sequence according to claim 3.

* * * * *